United States Patent
Murphy et al.

(10) Patent No.: US 7,824,913 B2
(45) Date of Patent: Nov. 2, 2010

(54) BIOENGINEERED TISSUE CONSTRUCTS AND METHODS FOR PRODUCING AND USING THEREOF

(75) Inventors: Michael P. Murphy, Chelmsford, MA (US); Vincent Ronfard, West Newton, MA (US)

(73) Assignee: Organogenesis, Inc., Canton, MA (US)

(*) Notice: Subject to any disclaimer, the term of this patent is extended or adjusted under 35 U.S.C. 154(b) by 0 days.

(21) Appl. No.: 09/523,809

(22) Filed: Mar. 13, 2000

(65) Prior Publication Data

US 2002/0172705 A1 Nov. 21, 2002

Related U.S. Application Data

(63) Continuation of application No. PCT/US99/27505, filed on Nov. 19, 1999, which is a continuation-in-part of application No. 09/339,632, filed on Jun. 24, 1999, now abandoned.

(60) Provisional application No. 60/109,247, filed on Nov. 19, 1998.

(51) Int. Cl.
C12N 5/071 (2010.01)
C12N 5/00 (2006.01)
C12N 5/02 (2006.01)

(52) U.S. Cl. ............ 435/371; 435/375; 435/366; 435/402

(58) Field of Classification Search ........... 424/422, 424/423, 93.1, 93.2, 572; 435/320.1, 325, 435/371, 373, 69.1, 455
See application file for complete search history.

(56) References Cited

U.S. PATENT DOCUMENTS

| | | | |
|---|---|---|---|
| 4,485,096 A * | 11/1984 | Bell | 424/95 |
| 4,963,489 A | 10/1990 | Naughton et al. | |
| 5,032,508 A | 7/1991 | Naughton et al. | |
| 5,266,480 A * | 11/1993 | Naughton et al. | 435/371 |
| 5,374,515 A | 12/1994 | Parenteau et al. | |
| 5,443,950 A | 8/1995 | Naughton et al. | |
| 5,536,656 A | 7/1996 | Kemp et al. | 435/240.23 |
| 5,580,781 A | 12/1996 | Naughton et al. | |
| 5,618,284 A * | 4/1997 | Sand | 606/5 |
| 5,618,718 A | 4/1997 | Auger et al. | |
| 5,624,840 A | 4/1997 | Naughton et al. | |
| 5,667,961 A | 9/1997 | Bernard et al. | 435/1 |
| 5,712,163 A * | 1/1998 | Parenteau et al. | 435/405 |
| 5,716,404 A | 2/1998 | Vacanti et al. | |
| 5,753,267 A | 5/1998 | Badylak et al. | |
| 5,800,537 A | 9/1998 | Bell | |
| 6,733,530 B1 * | 5/2004 | Lam et al. | 623/15.12 |
| 2008/0108134 A1 * | 5/2008 | Murphy et al. | 435/371 |

FOREIGN PATENT DOCUMENTS

EP 0 282 746 9/1988
WO WO95/31473 11/1995

OTHER PUBLICATIONS

Jahoda et al. J Invest Dermatology. 101: 584-590, Oct. 1993.*
Garlick et al. Rev Oral Biol Med. 7(3): 204-221, 1996.*
Minuth et al. Cell and Tissue Research. 291(1): 1-11, Jan. 1998.*
Schinstine et al. Brain Research. Molecular Brain Research. 47(1-2): 195-201, Jul. 1997.*
Biegel et al. In Vitro Cell Dev Biol Anim. 30A(9): 581-8, Sep. 1994.*
Fitzpatrick et al., Dermatology in General Medicine. vol. 1, 4th Ed. pp. 117-119, 1993.*
Transwell-COL Collagen-Coated Membrane and Transwell Inserts & Dishes. http://www.corninglabware.com/, Sep. 2000.*
Naughton et al, Science 295:1009-1014, 2002.*
Fleishmajer et al, J. Histochem Cytochem 41(9):1359-66, 1993.*
Ghalbzouri et al, J Invest Dermatol. 124(1):79-86, 2005.*
Lee DY et al J Dermatol Sci. 43(2):95-104, 2006.*
Lee et al, Arch Dermatol Res. 296(7):296-302, 2005.*
Auquer at al, In Vitro Cell Dev Biol Anim. 36(2):96-103, 2000.*
Cohen et al., Annals of Biomedical Engineering, vol. 19, No. 5, pp. 600-601, "Tear strength properties of a novel cultured dermal tissue model", Document No. XP000892385.
PCT International Search Report Corresponding to International Application No. PCT/US99/27505; Authorized Officer: Ceder, O.; Date of Mailing: Mar. 22, 2000 (7 pages).
L'heureux, et al., "A Completely Biological Tissue-Engineered Human Blood Vessel", FASEB J. 12: 47-56, Jan. 1998.
Bateman et al., Biochem. J., "Cell-layer-associated proteolytic cleavage of the telopeptides . . . ", 245:677-682 (1987).
Bateman et al., J. Biol. Chem., "Induction of Procollagen Processing in Fibroblast Cultures by Neutral Polymers", 261:4198-4203 (1986).
Biegel et al., In Vitro Cell Dev. Biol., "Growth of Brain Microvessel . . . ", 30A:581-88 (1994).
Bottenstein et al., Methods in Enzymology, "The Growth of Cells in Serum-Free Hormone-Supplemented Media", 58:94-109 (1979).
Chan et al., Biochem. J., "Regulation of procollagen synthesis and processing . . . ", 269:175-181 (1990).
Fitzpatrick et al., Dermatology in General Medicine, vol. 1, 4th ed., pp. 117-119 (1993).
Garlick et al., Crit. Rev. Oral Biol. Med., "Keratinocyte Gene Transfer and Gene Therapy", 7:204-221 (1996).
Goldberg et al., Experimental Cell Research, "Collagen Formation in Vitro by Established . . . ", 31:444-447 (1963).
Grinnell et al., Exp. Cell Research, "Collagen Processing, Crosslinking, and Fibril Bundle Assembly . . . ", 181:483-491 (1989).
Ham et al., Methods in Enzymology, "Media and Growth Requirements", 58:44-93 (1979).

(Continued)

*Primary Examiner*—Michael Burkhart
(74) *Attorney, Agent, or Firm*—Foley Hoag, LLP

(57) ABSTRACT

Cultured tissue constructs comprising cultured cells and endogenously produced extracellular matrix components without the requirement of exogenous matrix components or network support or scaffold members. Some tissue constructs of the invention are comprised of multiple cell layers or more than one cell type. The tissue constructs of the invention have morphological features and functions similar to tissues their cells are derived and their strength makes them easily handleable. Preferred cultured tissue constructs of the invention are prepared in defined media, that is, without the addition of chemically undefined components.

5 Claims, 4 Drawing Sheets

OTHER PUBLICATIONS

Hata et al., Journal of Cellular Physiology, "L-Ascorbic Acid 2-Phosphate Stimulates Collagen . . . ", 138:8-16 (1989).

Ishikawa et al., British Journal of Dermatology, "Morphological. and biochemical analyses on fibroblasts . . . ", 136:6-11 (1997).

Jahoda et al., J. Invest. Dermatol., 101:584-590 (1993).

Minuth et al., Cell Tissue Res., "Tissue engineering: generation . . . ", 291:1-11 (1998).

Pardes et al., J. of Investigative Dermatology, 100:549 (1993).

Raghow et al., J. Clin. Invest., "Transforming Growth Factor-Beta Increases Steady State Levels . . . ", 79:1285-1288 (1987).

Ramshaw et al., Analytical Biochemistry, "Precipitation of Collagens by Polyethelene Glycols", 141:361-365 (1984).

Rubin et al., Journal of Cellular Physiology, "Coordination of Keratinocyte Programming in Human . . . ", 138:208-214 (1989).

Schinstine et al., Molecular Brain Research, "Potential effect of cytokines on trangene . . . ", 47:195-201 (1997).

Schwartz et al., J. Cell Biol., "Changes in the Components of Extracellular Matrix and in . . . ", 92:462-470 (1982).

Shivakumar et al., J. Mol. Cell Cardiol., "Paradoxical Effect of Cerium on Collagen Synthesis in Cardiac Fibroblasts", 24:775-780 (1992).

Transwell-COL Collagen-Coated Membrane and Transwell Inserts & Dishes. http://www.corninglabware.com/ (Sep. 2000).

Tsao and Young, "Letter to the Editor—Molecular Structure-Dependent Cyrtotoxic Effect of Ascorbate Derivatives," In Vitro Cell. Dev. Biol. 31:87-90 (1995).

* cited by examiner

3A

3B

BIOENGINEERED TISSUE CONSTRUCTS AND METHODS FOR PRODUCING AND USING THEREOF

CROSS-REFERENCE TO RELATED APPLICATIONS

This application is a continuation of international application number PCT/US99/27505, filed Nov. 19, 1999, which is a continuation-in-part of U.S. Ser. No. 09/339,632, filed Jun. 24, 1999, now abandoned, which claims the benefit of 60/109,247, filed Nov. 19, 1998.

FIELD OF THE INVENTION

The invention is in the field of tissue engineering. This invention is directed to an in vitro method for inducing cells to produce an extracellular matrix. This living extracellular matrix, which has tissue-like properties, can be used for testing or clinical purposes.

BACKGROUND OF THE INVENTION

The field of tissue engineering combines bioengineering methods with the principles of life sciences to understand the structural and functional relationships in normal and pathological mammalian tissues. The goal of tissue engineering is the development and ultimate application of biological substitutes to restore, maintain, or improve tissue functions. Thus, through tissue engineering, it is possible to design and manufacture a bioengineered tissue in a laboratory. Bioengineered tissues can include cells that are usually associated with a native mammalian or human tissues and synthetic or exogenous matrix scaffolds. The new bioengineered tissue must be functional when grafted onto a host, and be permanently incorporated within the host's body or progressively bioremodeled by cells from the recipient host patient. Fabrication of a tissue equivalent without a support member or scaffold leads to scientific challenges in creating the new bioengineered tissue.

SUMMARY OF THE INVENTION

The invention is directed to bioengineered tissue constructs of cultured cells and endogenously produced extracellular matrix components without the requirement of exogenous matrix components or network support or scaffold members. The invention can thus advantageously be made entirely from human cells, and human matrix components produced by those cells, for example, when the bioengineered tissue construct is designed for use in humans.

The invention is also directed to methods for producing tissue constructs by stimulation of cells in culture, such as fibroblasts, to produce extracellular matrix components without the addition of either exogenous matrix components, network support, or scaffold members.

The invention is also directed to methods for producing tissue constructs by stimulation of cells in culture, such as fibroblasts, to produce extracellular matrix components in a defined medium system and/or without the use of undefined or non-human-derived biological components, such as bovine serum or organ extracts.

Further, this tissue construct can be made by serial seedings of different cell types to produce a cultured tissue construct that mimics the cell composition and tissue structures of native tissues.

Still further, the tissue construct is produced and self-assembled by cultured cells without the need for scaffold support or the addition of exogenous extracellular matrix components.

The strength characteristics of the tissue constructs make it handleable for it to be easily and peelably removed from the culture apparatus in which it is formed and directly transplanted without the need for any support or carrier in clinical or testing applications.

The tissue constructs of the invention are useful for clinical purposes such as grafting to a patient with tissue or organ defect, such as skin ulcer or wound, or for in vitro tissue testing or animal grafting such as for safety testing or validation of pharmaceutical cosmetic, and chemical products.

DESCRIPTION OF THE FIGURES

FIG. 3A is a 7600× magnification showing endogenous matrix including alignment of collagen fibers between the fibroblasts. FIG. 3B is a 19000× magnification of fully formed endogenous collagen fibers demonstrating fibril arrangement and packing.

DETAILED DESCRIPTION OF THE INVENTION

Figure 1:
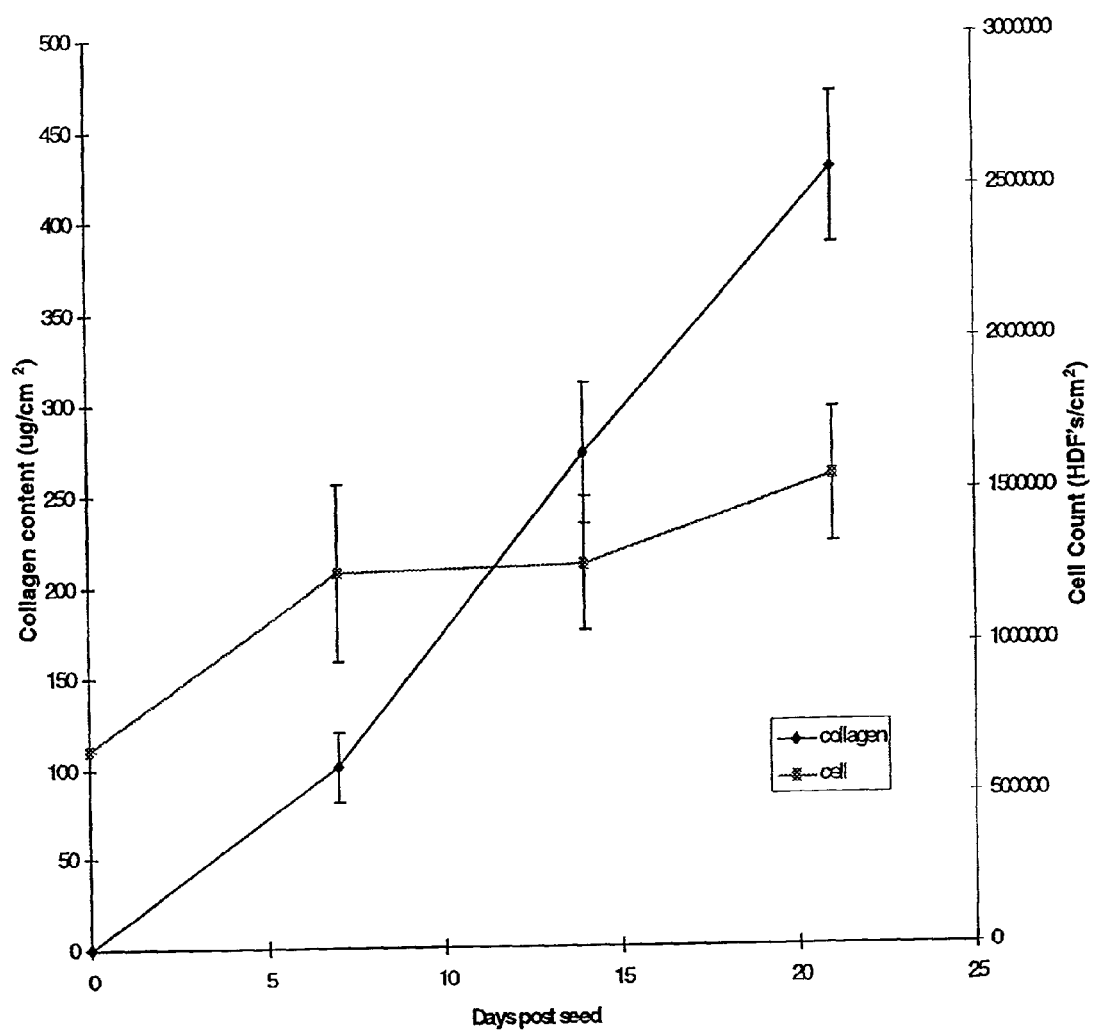
FIG. 1 is a graph depicting the increase in collagen concentration as determined by hydroxyproline assay as compared to the cell number in the human neonatal foreskin cell derived dermal construct described in Example 1.

Heretofore, current engineered living tissue constructs are not completely cell assembled and must rely on either the addition or incorporation of exogenous matrix components or synthetic members for structure or support, or both.

The bioengineered tissue constructs described herein exhibit many of the native features of the tissue from which their cells are derived. The tissue constructs thus produced can be used for grafting to a patient or for in vitro testing.

One preferred embodiment is a cell-matrix construct comprising a first cell type and endogenously produced extracellular matrix wherein the first cell type is capable of synthesizing and secreting extracellular matrix to produce the cell-matrix construct.

Another preferred embodiment is a bilayer construct comprising a first cell type and endogenously produced extracellular matrix and a layer of cells of a second type disposed thereon or within the cell-matrix construct formed by the first cell type.

A more preferred embodiment is a cell-matrix construct comprising fibroblasts, such as those derived from dermis, to form a cultured dermal construct.

Another more preferred embodiment is a cell-matrix construct comprising fibroblasts, such as those derived from dermis, to form a cultured dermal construct with a layer of keratinocytes cultured thereon to form an epidermal layer to result in a cultured bilayer skin construct. The cultured skin constructs of the invention express many physical morphological, and biochemical features of native skin.

In an even more preferred embodiment, the cell-matrix construct is a tissue construct that is similar to the dermal layer of skin, a human dermal construct, that is formed in a defined system comprising human-derived cells utilizing no chemically undefined components during its culture.

In the most preferred embodiment, the tissue constructs of the invention are fabricated in a chemically defined system comprising human-derived cells but no chemically undefined or non-human biological components or cells.

One preferred embodiment of the invention comprises a structural layer of at least one type of extracellular matrix-producing cells and endogenously produced extracellular matrix components, more simply termed "matrix", wherein the matrix is completely cell-synthesized and assembled by culturing the cells. This layer is herein termed a "cell-matrix construct" or a "cell-matrix layer" because the cells secrete and contain themselves within and through their matrix. The cultured tissue constructs do not require, thus do not include, exogenous matrix components, that is, matrix components not produced by the cultured cells but introduced by other means. In a more preferred embodiment, the cell-matrix construct produced by human dermal fibroblasts is shown to have a predominant concentration of collagen similar to native skin. As evidenced by electron microscopy, the matrix is fibrous in nature comprising collagen that exhibits the quarter-staggered 67 nm banding pattern, as well as packing organization of fibrils and fibril bundles similar to native collagen. Delayed reduction SDS-PAGE has detected the presence of both type I and type III collagen in these constructs, the predominant collagen types found in native human skin. Using standard immunohistochemistry (IHC) techniques, the dermal cell-matrix construct stains positively for decorin, a dermatan sulfate proteoglycan known to be associated with collagen fibrils and believed to regulate fibril diameter in vivo. Decorin can also be visualized in the construct with TEM. The produced tissue also stains positive for tenascin, an extracellular matrix glycoprotein found, for example, in mesenchyme or tissues under repair. Much like tissue under repair in vivo, the tissue produced in culture has been shown to increase its ratio of type I to type III collagen as the matrix is formed. While not wishing to be bound by theory, it is believed that the cells fill in the open space between them quickly with a loose matrix analogous to granulation tissue comprised of mostly type III collagen and fibronectin, and then remodel this loose matrix with a denser matrix comprised of mostly type I collages. The produced cell-matrix has been shown to contain glycosaminoglycans (GAG), such as hyaluronic acid (HA); fibronectin; proteoglycans besides decorin such as biglycan and versican; and, a profile of sulfated glycosaminoglycans such as di-hyaluronic acid; di-chondroitin-0-sulfate; di-chondroitin-4-sulfate; di-chondroitin-6-sulfate; di-chondroitin-4,6-sulfate; di-chondroitin-4-sulfate-UA-2S; and di-chondroitin-6-sulfate-UA-2S. These structural and biochemical features exhibit themselves as the construct develops in culture and are distinctively evident when the construct approaches its final form. The presence of these components in fully formed cultured dermal cell-matrix construct indicates that the construct has structural and biochemical features approaching that of normal dermis.

While the aforementioned list is a list of biochemical and structural features in a cultured cell-matrix construct formed from dermal fibroblasts, it should be recognized that cultured cell-matrix constructs formed from other types of fibroblasts will produce many of these features and others phenotypic for a tissue type from which they originated. In some cases, fibroblasts can be induced to express non-phenotypic components by either chemical exposure or contact, physical stresses, or by transgenic means. Another preferred embodiment of the invention is a cell-matrix layer having a second layer of cells disposed thereon. The second layer of cells is cultured on the cell-matrix layer to form a bioengineered bilayered tissue construct. In a more preferred embodiment, the cells of the second layer are of epithelial origin. In the most preferred embodiment, the second layer comprises cultured human keratinocytes that together with a first cell-matrix layer, a cell-matrix construct formed from dermal fibroblasts and endogenous matrix to form a dermal layer, comprise a living skin construct. When fully formed, the epidermal layer is a multilayered, stratified, and well-differentiated layer of keratinocytes that exhibit a basal layer, a suprabasal layer, a granular layer and a stratum corneum. The skin construct has a well-developed basement membrane present at the dermal-epidermal junction as exhibited by transmission electron microscopy (TEM). The basement membrane appears thickest around hemidesmosomes, marked by anchoring fibrils that are comprised of type VII collagen, as visualized by TEM. The anchoring fibrils can seen exiting from the basement membrane and entrapping the collagen fibrils in the dermal layer. These anchoring fibrils, as well as other basement membrane components, are secreted by keratinocytes. It is also known that while keratinocytes are capable of secreting basement membrane components on their own, a recognizable basement membrane will not form in the absence of fibroblasts. Immunohistochemical staining of the skin construct of the present invention has also shown that laminin, a basement membrane protein is present.

In a preferred method of the invention for forming a cell-matrix construct, a first cell type, an extracellular matrix-producing cell type, is seeded to a substrate, cultured, and induced to synthesize and secrete an organized extracellular matrix around them to form a cell-matrix construct. In another preferred method of the invention, a surface of the cell-matrix construct is seeded with cells of a second cell type and are cultured to form bilayered tissue construct. In a more preferred method, a full thickness skin construct having features similar to native human skin is formed by culturing fibroblasts, such as human dermal fibroblasts, under conditions sufficient to induce matrix synthesis to form a cell-matrix of dermal cells and matrix, a dermal layer, onto which human epithelial cells, such as keratinocytes, are seeded and cultured under conditions sufficient to form a fully differentiated stratified epidermal layer.

Therefore, one method of obtaining the tissue constructs of the present invention comprises:

(a) culturing at least one extracellular matrix-producing cell type in the absence of exogenous extracellular matrix components or a structural support member; and, (b) stimulating the cells of step (a) to synthesize, secrete, and organize extracellular matrix components to form a tissue-construct comprised of cells and matrix synthesized by those cells; wherein steps (a) and (b) may be done simultaneously or consecutively.

To form a bilayer tissue construct comprising a cell-matrix construct and a second cell layer thereon, the method additionally comprises the step of: (c) culturing cells of a second type on a surface of the formed tissue-construct to produce a bilayered tissue construct.

An extracellular matrix-producing cell type for use in the invention may be any cell type capable of producing and secreting extracellular matrix components and organizing the extracellular matrix components to form a cell-matrix construct. More than one extracellular matrix-producing cell type may be cultured to form a cell-matrix construct. Cells of different cell types or tissue origins may be cultured together as a mixture to produce complementary components and structures similar to those found in native tissues. For example, the extracellular matrix-producing cell type may have other cell types mixed with it to produce an amount of extracellular matrix that is not normally produced by the first cell type. Alternatively, the extracellular matrix-producing cell type may also be mixed with other cell types that form specialized tissue structures in the tissue but do not substantially contribute to the overall formation of the matrix aspect of the cell-matrix construct, such as in certain skin constructs of the invention.

While any extracellular matrix-producing cell type may be used in accordance with this invention, the preferred cell types for use in this invention are derived from mesenchyme. More preferred cell types are fibroblasts, stromal cells, and other supporting connective tissue cells, most preferably human dermal fibroblasts found in human dermis for the production of a human dermal construct. Fibroblast cells, generally, produce a number of extracellular matrix proteins, primarily collagen. There are several types of collagens produced by fibroblasts, however, type I collagen is the most prevalent in vivo. Human fibroblast cell strains can be derived from a number of sources, including, but not limited to neonate male foreskin, dermis, tendon, lung, umbilical cords, cartilage, urethra, corneal stroma, oral mucosa, and intestine. The human cells may include but need not be limited to fibroblasts, but may include: smooth muscle cells, chondrocytes and other connective tissue cells of mesenchymal origin. It is preferred, but not required, that the origin of the matrix-producing cell used in the production of a tissue construct be derived from a tissue type that it is to resemble or mimic after employing the culturing methods of the invention. For instance, in the embodiment where a skin-construct is produced, the preferred matrix-producing cell is a fibroblast, preferably of dermal origin. In another preferred embodiment, fibroblasts isolated by microdissection from the dermal papilla of hair follicles can be used to produce the matrix alone or in association with other fibroblasts. In the embodiment where a corneal-construct is produced, the matrix-producing cell is derived from corneal stroma. Cell donors may vary in development and age. Cells may be derived from donor tissues of embryos, neonates, or older individuals including adults. Embryonic progenitor cells such as mesenchymal stem cells may be used in the invention and induced to differentiate to develop into the desired tissue.

Although human cells are preferred for use in the invention, the cells to be used in the method of the invention are not limited to cells from human sources. Cells from other mammalian species including, but not limited to, equine, canine, porcine, bovine, and ovine sources; or rodent species such as mouse or rat may be used. In addition, cells that are spontaneously, chemically or virally transfected or recombinant cells or genetically engineered cells may also be used in this invention. For those embodiments that incorporate more than one cell type, chimeric mixtures of normal cells from two or more sources; mixtures of normal and genetically modified or transfected cells; or mixtures of cells of two or more species or tissue sources may be used.

Recombinant or genetically-engineered cells may be used in the production of the cell-matrix construct to create a tissue construct that acts as a drug delivery graft for a patient needing increased levels of natural cell products or treatment with a therapeutic. The cells may produce and deliver to the patient via the graft recombinant cell products, growth factors, hormones, peptides or proteins for a continuous amount of time or as needed when biologically, chemically, or thermally signaled due to the conditions present in the patient. Either long or short-term gene product expression is desirable, depending on the use indication of the cultured tissue construct. Long term expression is desirable when the cultured tissue construct is implanted to deliver therapeutic products to a patient for an extended period of time. Conversely, short term expression is desired in instances where the cultured tissue construct is grafted to a patient having a wound where the cells of the cultured tissue construct are to promote normal or near-normal healing or to reduce scarification of the wound site. Once the wound has healed, the gene products from the cultured tissue construct are no longer needed or may no longer be desired at the site. Cells may also be genetically engineered to express proteins or different types of extracellular matrix components which are either 'normal' but expressed at high levels or modified in some way to make a graft device comprising extracellular matrix and living cells that is therapeutically advantageous for improved wound healing, facilitated or directed neovascularization, or minimized scar or keloid formation. These procedures are generally known in the art, and are described in Sambrook et al, *Molecular Cloning, A Laboratory Manual*, Cold Spring Harbor Press, Cold Spring Harbor, N.Y. (1989), incorporated herein by reference. All of the above-mentioned types of cells are included within the definition of a "matrix-producing cell" as used in this invention.

The predominant major extracellular matrix component produced by fibroblasts is fibrillar collagen, particularly collagen type I. Fibrillar collagen is a key component in the cell-matrix structure; however, this invention is not to be limited to matrices comprised of only this protein or protein type. For instance, other collagens, both fibrillar and non-fibrillar collagen from the collagen family such as collagen types II, III, IV, V, VI, VII, VIII, IX, X, XI, XII, XIII, XIV, XV, XVI, XVII, XVIII, XIX, may be produced by use of the appropriate cell type. Similarly, other matrix proteins which can be produced and deposited using the current method include, but are not limited to elastin; proteoglycans such as decorin or biglycan; or glycoproteins such as tenascin; vitronectin; fibronectin; laminin, thrombospondin I, and glycosaminoglycans (GAG) such as hyaluronic acid (HA).

The matrix-producing cell is cultured in a vessel suitable for animal cell or tissue culture, such as a culture dish, flask, or roller-bottle, which allows for the formation of a three-dimensional tissue-like structure. Suitable cell growth surfaces on which the cells can be grown can be any biologically compatible material to which the cells can adhere and provide an anchoring means for the cell-matrix construct to form. Materials such as glass; stainless steel; polymers, including polycarbonate, polystyrene, polyvinyl chloride, polyvinylidene, polydimethylsiloxane, fluoropolymers, and fluorinated ethylene propylene; and silicon substrates, including fused silica, polysilicon, or silicon crystals may be used as a cell growth surfaces. The cell growth surface material may be chemically treated or modified, electrostatically charged, or coated with biologicals such as poly-1-lysine or peptides. An example of a peptide coating is RGD peptide.

While the tissue construct of the invention may be grown on a solid cell growth surface, a cell growth surface with pores that communicate both top and bottom surfaces of the membrane to allow bilateral contact of the medium to the developing tissue construct or for contact from only below the culture is preferred. Bilateral contact allows medium to contact both the top and bottom surfaces of the developing construct for maximal surface area exposure to the nutrients contained in the medium. Medium may also contact only the bottom of the forming cultured tissue construct so that the top surface may be exposed to air, as in the development of a cultured skin construct. The preferred culture vessel is one that utilizes a carrier insert, a culture-treated permeable member such as a porous membrane that is suspended in the culture vessel containing medium. Typically, the membrane is secured to one end of a tubular member or framework that is inserted within and interfaces with a base, such as a petri or culture dish that can be covered with a lid. Culture vessels incorporating a carrier insert with a porous membrane are known in the art and are preferred for carrying out the invention and are described in a number United States patents in the field, some of which have been made commercially available, including for instance: U.S. Pat. Nos. 5,766,937, 5,466,602, 5,366,893, 5,358,871, 5,215,920, 5,026,649, 4,871,674, 4,608,342, the disclosures of which are incorporated herein. When these types of culture vessels are employed, the tissue-construct is produced on one surface of the membrane, preferably the top, upwardly facing surface and the culture is contacted by cell media on both top and bottom surfaces. The pores in the growth surface allow for the passage of culture media for providing nutrients to the underside of the culture through the membrane, thus allowing the cells to be fed bilaterally or solely from the bottom side. A preferred pore size is one that is small enough that it does not allow for the growth of cells through the membrane, yet large enough to allow for free passage of nutrients contained in culture medium to the bottom surface of the cell-matrix construct, such as by capillary action. Preferred pore sizes are about less than 3 microns but range between about 0.1 microns to about 3 microns, more preferably between about 0.2 microns to about 1 micron and most preferably about 0.4 micron to about 0.6 micron sized pores are employed. In the case of human dermal fibroblasts, the most preferred material is polycarbonate having a pore size is between about 0.4 to about 0.6 microns. The maximum pore size depends not only on the size of the cell but also the ability of the cell to alter its shape and pass through the membrane. It is important that the tissue-like construct adheres to the surface but does not incorporate or envelop the substrate so it is removable from it such as by peeling with minimal force. The size and shape of the tissue construct formed is dictated by the size of the vessel surface or membrane on which it grown. Substrates may be round or angular or shaped with rounded corner angles, or irregularly shaped. Substrates may also be flat or contoured as a mold to produce a shaped construct to interface with a wound or mimic the physical structure of native tissue. To account for greater surface areas of the growth substrate, proportionally more cells are seeded to the surface and a greater volume of media is needed to sufficiently bathe and nourish the cells. When the tissue construct is finally formed, whether it is a single layer cell-matrix construct or a bilayer construct, it is removed by peeling from the membrane substrate before grafting to a patient.

The cultured tissue constructs of the invention do not rely on synthetic or bioresorbable members, such as a mesh member for the formation of the tissue constructs. The mesh member is organized as a woven, a knit, or a felt material. In systems where a mesh member is employed, the cells are cultured on the mesh member and growing on either side and within the interstices of the mesh to envelop and incorporate the mesh within the cultured tissue construct. The final construct formed by methods that incorporate such a mesh rely on it for physical support and for bulk. Examples of cultures tissue constructs that rely on synthetic mesh members are found in U.S. Pat. Nos. 5,580,781, 5,443,950, 5,266,480, 5,032,508, 4,963,489 to Naughton, et al.

The system for the production of the cell-matrix layer may be either static or may employ a perfusion means to the culture media. In the static system, the culture medium is still and relatively motionless as contrasted to the perfusion system where the medium is in motion. The perfusion of medium affects the viability of the cells and augments the development of the matrix layer. Perfusion means include, but are not limited to: using a magnetic stirbar or motorized impeller in the culture dish subjacent (below) or adjacent to the substrate carrier containing the culture membrane to stir the medium; pumping medium within or through the culture dish or chamber; gently agitating the culture dish on a shaking or rotating platform; or rolling, if produced in a roller bottle. Other perfusion means can be determined by one skilled in the art for use in the method of the invention.

Culture media formulations suitable for use in the present invention are selected based on the cell types to be cultured and the tissue structure to be produced. The culture medium that is used and the specific culturing conditions needed to promote cell growth, matrix synthesis, and viability will depend on the type of cell being grown.

In some instances, such as in the fabrication of bioengineered bilayer skin constructs of the present invention, the media composition varies with each stage of fabrication as different supplementation is necessary for different purposes. In a preferred method, the cell-matrix layer is formed under defined conditions, that is, cultured in chemically defined media. In another preferred method, a tissue construct comprises a cell-matrix layer provided with a second layer of cells disposed and cultured thereon wherein both cell types are cultured in a defined culture media system. Alternatively, the tissue construct comprises a cell-matrix layer fabricated under defined media conditions and a second layer formed thereon under undefined media conditions. In the converse, the tissue construct comprises a cell-matrix layer may be fabricated under undefined media conditions and the second layer formed thereon under defined media conditions.

The use of chemically defined culture media is preferred, that is, media free of undefined animal organ or tissue extracts, for example, serum, pituitary extract, hypothalamic extract, placental extract, or embryonic extract or proteins and factors secreted by feeder cells. In a most preferred embodiment, the media is free of undefined components and defiled biological components derived from non-human sources. Although the addition of undefined components is not preferred, they may be used in accordance with the disclosed methods at any point in culture in order to fabricate successfully a tissue construct. When the invention is carried out utilizing screened human cells cultured using chemically defined components derived from no non-human animal sources, the resultant tissue construct is a defined human tissue construct. Synthetic functional equivalents may also be added to supplement chemically defined media within the purview of the definition of chemically defined for use in the most preferred fabrication method. Generally, one of skill in the art of cell culture will be able to determine suitable natural human, human recombinant, or synthetic equivalents to commonly known animal components to supplement the culture media of the invention without undue investigation or experimentation. The advantages in using such a construct in the clinic is that the concern of adventitious animal or cross-species virus contamination and infection is diminished. In the testing scenario, the advantages of a chemically defined construct is that when tested, there is no chance of the results being confounded due to the presence of the undefined components.

Culture medium is comprised of a nutrient base usually further supplemented with other components. The skilled artisan can determine appropriate nutrient bases in the art of animal cell culture with reasonable expectations for successfully producing a tissue construct of the invention. Many commercially available nutrient sources are useful on the practice of the present invention. These include commercially available nutrient sources which supply inorganic salts, an energy source, amino acids, and B-vitamins such as Dulbecco's Modified Eagle's Medium (DMEM); Minimal Essential Medium (MEM); M199; RPMI 1640; Iscove's Modified Dulbecco's Medium (EDMEM). Minimal Essential Medium (MEM) and M199 require additional supplementation with phospholipid precursors and non-essential amino acids. Commercially available vitamin-rich mixtures that supply additional amino acids, nucleic acids, enzyme cofactors, phospholipid precursors, and inorganic salts include Ham's F-12, Ham's F-10, NCTC 109, and NCTC 135. Albeit in varying concentrations, all basal media provide a basic nutrient source for cells in the form of glucose, amino acids, vitamins, and inorganic ions, together with other basic media components. The most preferred base medium of the invention comprises a nutrient base of either calcium-free or low calcium Dulbecco's Modified Eagle's Medium (DMEM), or, alternatively, DMEM and Ham's F-12 between a 3-to-1 ratio to a 1-to-3 ratio, respectively.

The base medium is supplemented with components such as amino acids, growth factors, and hormones. Defined culture media for the culture of cells of the invention are described in U.S. Pat. No. 5,712,163 to Parenteau and in International PCT Publication No. WO 95/31473, the disclosures of which are incorporated herein by reference. Other media are known in the art such as those disclosed in Ham and McKeehan, Methods in Enzymology, 58:44-93 (1979), or for other appropriate chemically defined media, in Bottenstein et al, Methods in Enzymology, 58:94-109 (1979). In the preferred embodiment, the base medium is supplemented with the following components known to the skilled artisan in animal cell culture: insulin, transferrin, triiodothyronine (T3), and either or both ethanolamine and o-phosphoryl-ethanolamine, wherein concentrations and substitutions for the supplements may be determined by the skilled artisan.

Insulin is a polypeptide hormone that promotes the uptake of glucose and amino acids to provide long term benefits over multiple passages. Supplementation of insulin or insulin-like growth factor (IGF) is necessary for long term culture as there will be eventual depletion of the cells' ability to uptake glucose and amino acids and possible degradation of the cell phenotype. Insulin may be derived from either animal, for example bovine, human sources, or by recombinant means as human recombinant insulin. Therefore, a human insulin would qualify as a chemically defined component not derived from a non-human biological source. Insulin supplementation is advisable for serial cultivation and is provided to the media at a wide range of concentrations. A preferred concentration range is between about 0.1 µg/ml to about 500 µg/ml, more preferably at about 5 µg/ml to about 400 µg/ml, and most preferably at about 375 µg/ml. Appropriate concentrations for the supplementation of insulin-like growth factor, such as IGF-1 or IGF-2, may be easily determined by one of skill in the art for the cell types chosen for culture.

Transferrin is in the medium for iron transport regulation. Iron is an essential trace element found in serum. As iron can be toxic to cells in its free form, in serum it is supplied to cells bound to transferrin at a concentration range of preferably between about 0.05 to about 50 µg/ml, more preferably at about 5 µg/ml.

Triiodothyronine (T3) is a basic component and is the active form of thyroid hormone that is included in the medium to maintain rates of cell metabolism. Triiodothyronine is supplemented to the medium at a concentration range between about 0 to about 400 pM, more preferably between about 2 to about 200 pM and most preferably at about 20 pM.

Either or both ethanolamine and o-phosphoryl-ethanolamine, which are phospholipids, are added whose function is an important precursor in the inositol pathway and fatty acid metabolism. Supplementation of lipids that are normally found in serum is necessary in a serum-free medium. Ethanolamine and o-phosphoryl-ethanolamine are provided to media at a concentration range between about $10^{-6}$ to about $10^{-2}$ M, more preferably at about $1 \times 10^{-4}$ M.

Throughout the culture duration, the base medium is additionally supplemented with other components to induce synthesis or differentiation or to improve cell growth such as hydrocortisone, selenium, and L-glutamine.

Hydrocortisone has been shown in keratinocyte culture to promote keratinocyte phenotype and therefore enhance differentiated characteristics such as involucrin and keratinocyte transglutaminase content (Rubin et al., J. Cell Physiol., 138: 208-214 (1986)). Therefore, hydrocortisone is a desirable additive in instances where these characteristics are beneficial such as in the formation of keratinocyte sheet grafts or skin constructs. Hydrocortisone may be provided at a concentration range of about 0.01 ug/ml to about 4.0 µg/ml, most preferably between about 0.4 µg/ml to 16 ug/ml.

Selenium is added to serum-free media to resupplement the trace elements of selenium normally provided by serum. Selenium may be provided at a concentration range of about $10^{-9}$ M to about $10^{-7}$ M; most preferably at about $5.3 \times 10^{-8}$ M.

The amino acid L-glutamine is present in some nutrient bases and may be added in cases where there is none or insufficient amounts present. L-glutamine may also be provided in stable form such as that sold under the mark, GlutaMAX-1™ (Gibco BRL, Grand Island, N.Y.). GlutaMAX-1™ is the stable dipeptide form of L-alanyl-L-glutamine and may be used interchangeably with L-glutamine and is provided in equimolar concentrations as a substitute to L-glutamine. The dipeptide provides stability to L-glutamine from degradation over time in storage and during incubation that can lead to uncertainty in the effective concentration of L-glutamine in medium. Typically, the base medium is supplemented with preferably between about 1 mM to about 6 mM, more preferably between about 2 mM to about 5 mM, and most preferably 4 mM L-glutamine or GlutaMAX-1™.

Growth factors such as epidermal growth factor (EGF) may also be added to the medium to aid in the establishment of the cultures through cell scale-up and seeding. EGF in native form or recombinant form may be used. Human forms, native or recombinant, of EGF are preferred for use in the medium when fabricating a skin equivalent containing no non-human biological components. EGF is an optional component and may be provided at a concentration between about 1 to 15 ng/mL, more preferably between about 5 to 10 ng/mL.

The medium described above is typically prepared as set forth below. However, it should be understood that the components of the present invention may be prepared and assembled using conventional methodology compatible with their physical properties. It is well known in the art to substitute certain components with an appropriate analogous or functionally equivalent acting agent for the purposes of availability or economy and arrive at a similar result. Naturally occurring growth factors may be substituted with recombinant or synthetic growth factors that have similar qualities and results when used in the performance of the invention.

Media in accordance with the present invention are sterile. Sterile components are bought sterile or rendered sterile by conventional procedures, such as filtration, after preparation. Proper aseptic procedures were used throughout the following Examples. DMEM and F-12 are first combined and the individual components are then added to complete the medium. Stock solutions of all components can be stored at −20° C., with the exception of nutrient source that can be stored at 4° C. All stock solutions are prepared at 500× final concentrations listed above. A stock solution of insulin, transferrin and triiodothyronine (all from Sigma) is prepared as follows: triiodothyronine is initially dissolved in absolute ethanol in 1N hydrochloric acid (HCl) at a 2:1 ratio. Insulin is dissolved in dilute HCl (approximately 0.1N) and transferrin is dissolved in water. The three are then mixed and diluted in water to a 500× concentration. Ethanolamine and o-phosphoryl-ethanolamine are dissolved in water to 500× concentration and are filter sterilized. Progesterone is dissolved in absolute ethanol and diluted with water. Hydrocortisone is dissolved in absolute ethanol and diluted in phosphate buffered saline (PBS). Selenium is dissolved in water to 500× concentration and filter sterilized. EGF is purchased sterile and is dissolved in PBS. Adenine is difficult to dissolve but may be dissolved by any number of methods known to those skilled in the art. Serum albumin may be added to certain components in order to stabilize them in solution and are presently derived from either human or animal sources. For example, human serum albumin (HSA) or bovine serum albumin (BSA) may be added for prolonged storage to maintain the activity of the progesterone and EGF stock solutions. The medium can be either used immediately after preparation or, stored at 4° C. If stored, EGF should not be added until the time of use.

In order to form the cell-matrix layer by the culture of matrix-producing cells, the medium is supplemented with additional agents that promote matrix synthesis and deposition by the cells. These supplemental agents are cell-compatible, defined to a high degree of purity and are free of contaminants. The medium used to produce the cell-matrix layer is termed "matrix production medium".

To prepare the matrix production medium, the base medium is supplemented with an ascorbate derivative such as sodium ascorbate, ascorbic acid, or one of its more chemically stable derivatives such as L-ascorbic acid phosphate magnesium salt n-hydrate. Ascorbate is added to promote hydroxylation of proline and secretion of procollagen, a soluble precursor to deposited collagen molecules. Ascorbate has also been shown to be an important cofactor for post-translation processing of other enzymes as well as an upregulator of type I and type III collagen synthesis.

While not wishing to be bound by theory, supplementing the medium with amino acids involved in protein synthesis conserves cellular energy by not requiring the cells produce the amino acids themselves. The addition of proline and glycine is preferred as they, as well as the hydroxylated form of proline, hydroxyproline, are basic amino acids that make up the structure of collagen.

While not required, the matrix-production medium is optionally supplemented with a neutral polymer. The cell-matrix constructs of the invention may be produced without a neutral polymer, but again not wishing to be bound by theory, its presence in the matrix production medium may assist in collagen processing and deposition more consistently between samples. One preferred neutral polymer is polyethylene glycol (PEG), which has been shown to promote in vitro processing of the soluble precursor procollagen produced by the cultured cells to matrix deposited collagen. Tissue culture grade PEG within the range between about 1000 to about 4000 MW (molecular weight), more preferably between about 3400 to about 3700 MW is preferred in the media of the invention. Preferred PEG concentrations for use in the method may be at concentrations at about 5% w/v or less, preferably about 0.01% w/v to about 0.5% w/v, more preferably between about 0.025% w/v to about 0.2% w/v, most preferably about 0.05% w/v. Other culture grade neutral polymers such dextran, preferably dextran T-40, or polyvinylpyrrolidone (PVP), preferably in the range of 30,000-40,000 MW, may also be used at concentrations at about 5% w/v or less, preferably between about 0.01% w/v to about 0.5% w/v, more preferably between about 0.025% w/v to about 0.2% w/v, most preferably about 0.05% w/v. Other cell culture grade and cell-compatible agents that enhance collagen processing and deposition may be ascertained by the skilled routineer in the art of mammalian cell culture.

When the matrix producing cells are confluent, and the culture medium is supplemented with components that assist in matrix synthesis, secretion, or organization, the cells are said to be stimulated to form a tissue-construct comprised of cells and matrix synthesized by those cells.

Therefore, a preferred matrix production medium formulation comprises: a base 3:1 mixture of Dulbecco's Modified Eagle's Medium (DMEM) (high glucose formulation, without L-glutamine) and Hams F-12 medium supplemented with either 4 mM L-glutamine or equivalent, 5 ng/ml epidermal growth factor, 0.4 µg/ml hydrocortisone, $1\times10^{-4}$ M ethanolamine, $1\times10^{-4}$ M o-phosphoryl-ethanolamine, 5 µg/ml insulin, 5 µg/ml transferrin, 20 pM triiodothyronine, 6.78 ng/ml selenium, 50 ng/ml L-ascorbic acid, 0.2 µg/ml L-proline, and 0.1 µg/ml glycine. To the production medium, other pharmacological agents may be added to the culture to alter the nature, amount, or type of the extracellular matrix secreted. These agents may include polypeptide growth factors, transcription factors or inorganic salts to up-regulate collagen transcription. Examples of polypeptide growth factors include transforming growth factor-beta 1 (TGF-β1) and tissue-plasminogen activator (TPA), both of which are known to upregulate collagen synthesis. Raghow et al., Journal of Clinical Investigation, 79:1285-1288 (1987); Pardes et al., Journal of Investigative Dermatology, 100:549 (1993). An example of an inorganic salt that stimulates collagen production is cerium. Shivakumar et al., Journal of Molecular and Cellular Cardiology 24:775-780 (1992).

The cultures are maintained in an incubator to ensure sufficient environmental conditions of controlled temperature, humidity, and gas mixture for the culture of cells. Preferred conditions are between about 34° C. to about 38° C., more preferably 37±1° C. with an atmosphere between about 5-10±1% $CO_2$ and a relative humidity (Rh) between about 80-90%.

In the preferred embodiment, the cell-matrix construct is a dermal construct formed of dermal fibroblasts and their secreted matrix. Preferably, human dermal fibroblasts are used, derived as primary cells from dermis or more preferably from serially passaged or subcultured from established cell stocks or banks that have been screened against viral and bacterial contamination and tested for purity. Cells are cultured under sufficient conditions in growth medium to cause them to proliferate to an appropriate number for seeding the cells to the culture substrate on which to form a cell-matrix construct. Alternatively, cells from frozen cell stocks may be seeded directly to the culture substrate.

Once sufficient cell numbers have been obtained, cells are harvested and seeded onto a suitable culture surface and cultured under appropriate growth conditions to form a confluent sheet of cells. In the preferred embodiment, the cells are seeded on a porous membrane that is submerged to allow medium contact from below the culture through the pores and directly above. Preferably, cells are suspended in either base or growth media and are seeded on the cell culture surface at a density between about $1 \times 10^5$ cells/cm$^2$ to about $6.6 \times 10^5$ cells/cm$^2$, more preferably between about $3 \times 10^5$ cells/cm$^2$ to about $6.6 \times 10^5$ cells/cm$^2$ and most preferably at about $6.6 \times 10^5$ cells/cm$^2$ (cells per square centimeter area of the surface). Cultures are cultured in growth medium to establish the culture and are cultured to between about 80% to 100% confluence at which time they are induced chemically by changing the medium to matrix production medium in order to upregulate the synthesis and secretion of extracellular matrix. In an alternate method, cells are seeded directly in production media to eliminate the need to change from the basic media to the production media but it is a method that requires higher seeding densities.

During the culture, fibroblasts organize the secreted matrix molecules to form a three dimensional tissue-like structure but do not exhibit significant contractile forces to cause the forming cell-matrix construct to contract and peel itself from the culture substrate. Media exchanges are made every two to three days with fresh matrix production medium and with time, the secreted matrix increases in thickness and organization. The time necessary for creating a cell-matrix construct is dependent on the ability of the initial seeding density, the cell type, the age of the cell line, and the ability of the cell line to synthesize and secrete matrix. When fully formed, the constructs of the invention have bulk thickness due to the fibrous matrix produced and organized by the cells; they are not ordinary confluent or overly confluent cell cultures where the cells may be loosely adherent to each other. The fibrous quality gives the constructs cohesive tissue-like properties unlike ordinary cultures because they resist physical damage, such as tearing or cracking, with routine handling in a clinical setting. In the fabrication of a cultured dermal construct, the cells will form an organized matrix around themselves on the cell culture surface preferably at least about 30 microns in thickness or more, more preferably between about 60 to about 120 microns thick across the surface of the membrane; however, thicknesses have been obtained in excess of 120 microns and are suitable for use in testing or clinical applications where such greater thicknesses are needed.

In a more preferred method, an epithelial cell layer is applied to one surface, preferably the top, upwardly facing surface of the cell-matrix construct. To the cell-matrix construct, epithelial cells may be seeded and cultured thereon to form a multilayer tissue construct. In the most preferred method, keratinocytes derived from skin are grown on the cell construct to form a skin construct. In other preferred embodiments, corneal epithelial cells, also termed corneal keratinocytes, may be seeded on the cell-matrix construct to form a corneal construct. Epithelial cells from the oral mucosa may be grown on the cell-matrix construct to form a construct of oral mucosa. Epithelial cells from esophagus may be seeded on the cell-matrix construct to form a construct of esophageal tissue. Uroepithelial cells from the urogenital tract may be seeded on the cell-matrix construct to form a construct of uroepithelium. Other cells of epithelial origin may be selected to form a construct of tissue from which those cells were derived.

Methods for providing epidermal cells to a dermal substrate, and methods for their culture, including induction of differentiation and cornification to form a differentiated keratinocyte layer are known in the art and are described in U.S. Pat. No. 5,712,163 to Parenteau, et al. and in U.S. Pat. No. 5,536,656 to Kemp, et al., the contents of which are incorporated herein by reference. Typically to perform the epidermalization of the cell-matrix construct, keratinocytes are seeded to the cell-matrix construct and cultured thereon until the layer is about one to three cell layers thick. The keratinocytes are then induced to differentiate to form a multilayer epidermis and are then induced to cornify to form a stratum corneum.

In the method of forming a differentiated epidermal layer, subcultured keratinocytes are taken from the cell stock and their cell numbers are expanded. When a necessary number of cells have been obtained, they are released from the culture substrate, suspended, counted, diluted and then seeded to the top surface of the cell-matrix construct at a density between about $4.5 \times 10^3$ cells/cm$^2$ to about $5.0 \times 10^5$ cells/cm$^2$, more preferably between about $1.0 \times 10^4$ cells/cm$^2$ to about $1.0 \times 10^5$ cells/cm$^2$, and most preferably at about $4.5 \times 10^4$ cells/cm$^2$. The constructs are then incubated for between about 60 to about 90 minutes at $37 \pm 1°$ C., 10% $CO_2$ to allow the keratinocytes to attach. After the incubation, the constructs are submerged in epidermalization medium. After a sufficient length of time in culture, the keratinocytes proliferate and spread to form a confluent monolayer across the cell-matrix construct. Once confluent, the cell media formulation is changed to differentiation medium to induce cell differentiation. When a multilayer epithelium has formed, cornification media is then used and the culture is brought to the air-liquid interface. For the differentiation and cornification of keratinocytes, the cells are exposed to a dry or low humidity air-liquid interface. A dry or low-humidity interface can be characterized as trying to duplicate the low moisture levels of skin. With time, keratinocytes will express most or all keratins and other features found in native skin when exposed to these conditions.

As mentioned above, the system for the production of a cell-matrix construct may be used in the formation of a corneal construct. The corneal epithelial cells can be derived from a variety of mammalian sources. The preferred epithelial cell is a rabbit or human corneal epithelial cell (corneal keratinocyte) but any mammalian corneal keratinocyte may be used. Other epithelial keratinocytes such as those derived from the sclera (outer white opaque portion) of the eye or epidermis may be substituted, but corneal keratinocytes are preferable. In the method for forming a corneal construct, the medium is removed from the culture insert (containing the cell-matrix construct) and its surround. Normal rabbit corneal epithelial cells are expanded via subculture, trypsinized to remove them from the cultures substrate, suspended in culture medium, and seeded on top of the membrane at a density between about $7.2 \times 10^4$ to about $1.4 \times 10^5$ cells/cm$^2$. The constructs are then incubated without medium for about four hours at $37 \pm 1°$ C., 10% $CO_2$ to allow the epithelial cells to attach. After incubation, the constructs are submerged in Corneal Maintenance Medium (CMM) (Johnson et al., 1992.) The epithelial cells are cultured until the cell-matrix construct is covered with the epithelial cells. Completeness of epithelial coverage can be ascertained by a variety of methods, for illustration by staining the culture with a solution of Nile Blue sulfate (1:10,000 in phosphate buffered saline). Once the cell-matrix construct is covered, after approximately seven days, the constructs are aseptically transferred to new culturing trays with sufficient corneal maintenance medium (CMM) to achieve a fluid level just to the surface of the construct to maintain a moist interface without submersion of the epithelial layer. The constructs are incubated at 37±1° C., 10% $CO_2$, and greater than 60% humidity, with the CMM, making media changes, as necessary, typically, three times per week.

For the differentiation, but not the cornification of the epithelial cell layer, as necessary in the production of a corneal construct, the epithelial cell surface is exposed to a moist air-liquid interface. Methods for providing a moist air-liquid interface are described in U.S. Pat. No. 5,374,515 to Parenteau. As used herein, the term "moist interface" is intended to mean a culture environment which is regulated so that the surface of the construct is moist, with high humidity, but not dry or submerged. The exact level of moisture and humidity in the culture environment is not critical, but it should be sufficiently moist and humid to avoid the formation of cornified cells. A moist interface can be characterized as trying to duplicate similar moisture levels of the human eye.

In an alternate preferred embodiment, a seeding of a second matrix-producing cell may be performed on a first formed cell-matrix construct to obtain a thicker cell-matrix construct or a bilayer cell-matrix construct. The second seeding can be performed with the same cell type or strain or with a different cell type or strain, depending on the desired result. The second seeding is performed under the same conditions employing the procedures and matrix production medium used in the production of the first layer. One result in performing the second seeding with a different cell type is to have a matrix formed with different matrix component profiles or matrix packing density to affect wound healing when the construct is grafted to a patient. The first cell seeding produces a matrix analogous to the reticular layer of dermis, a more densely packed layer of Type I collagen and constituent extracellular matrix components. The second cell seeding would produce a matrix similar to the papillary layer of dermis characterized by looser collagen fibrils and extracellular matrix. Another result is that the second cell type may produce a therapeutic substance that would also affect wound healing, such as improved graft take or graft integration or the minimization or prevention of scar formation.

In another preferred embodiment, mixed cell populations of two or more cell types may be cultured together during the formation of a cell-matrix construct provided that at least one of the cell types used is capable of synthesizing extracellular matrix. The second cell type may be one needed to perform other tissue functions or to develop particular structural features of the tissue construct. For instance, in the production of a skin construct, dermal papilla cells or epithelial cells from adnexas may be cultured with the matrix-producing cells to allow the formation of epithelial appendages or their components. Epidermal appendages such as sweat or sebaceous gland structures or components or hair follicle structures or components may form when cultured together with the matrix-producing cells. Epithelial cells may be derived from the appendageal structures of gland and hair located in deep dermis, such as by microdissection, and include eccrine cells, myoepithelial cells, glandular secretory cells, hair follicle stem cells. Other cell types normally found in skin that constitute skin may also be added such as melanocytes, Langerhans cells, and Merkel cells. Similarly, vascular endothelial cells may be co-cultured to produce rudimentary components for new vasculature formation. Adipocytes may also be cultured with the matrix-producing cells to form a construct used for reconstructive surgery. As alternate mode of delivery of this second cell type, the cells may be locally seeded as a spot or as an arrangement of any number of spots of cells on or within a forming or completely formed cell-tissue matrix for localized development of these structures. To seed the cells within the cell-matrix construct, the cells may be injected between the top and bottom surfaces, within the cell-matrix, for the cells to grow, form specialized structures and perform their specialized function.

To produce a three-layered tissue construct, a first seeding of cells comprising a matrix-producing cell type or a non-matrix-producing cell type is seeded on the culture substrate for a time sufficient to produce a cell-matrix construct or a cell layer. Once the first cell-matrix construct or cell layer is formed, a second seeding of cells comprising a matrix-producing cell type is seeded on the top surface of the first cell-matrix construct or cell layer and cultured for a time under conditions sufficient to form a second cell-matrix construct on the first construct. On the second cell-matrix construct, a third seeding of a third cell type is seeded and cultured under sufficient conditions to produce the third layer. As an example, to produce a three-layer corneal construct, the cell of the first cell-type may be comprised of endothelial origin, such as corneal endothelial cells; the second cell type may comprise cells of connective tissue origin, such as corneal keratocytes; and the third cell type may comprise cells of epithelial origin, such as corneal epithelial cells. As another example of a three-layer construct of skin, the cell of the first seeding may be of vascular origin to provide components for vascularization, the cells of the second seeding may comprise dermal fibroblasts to form a cell-matrix construct to serve as a dermal construct, and the cells of the third seeding may be epidermal keratinocytes to form an epidermal layer.

Tissue constructs of the invention can be stored at cryogenic temperatures when vitrification or cryopreservation methods are employed. Methods for vitrification of tissue constructs are described in U.S. Pat. No. 5,518,878 and methods for cryopreservation are described in U.S. Pat. Nos. 5,689,961 and 5,891,617 and in International PCT Application WO 96/24018, the disclosures of which are incorporated herein by reference.

The skin constructs of this invention can be used in tissue test systems for in vitro toxicology tests. Test systems that incorporate skin constructs for testing purposes are described in U.S. Pat. No. 4,835,102 the disclosure of which is incorporated herein by reference. Because the cell produced skin construct has similar structure, and, more importantly, a similar organization to skin, it can be a valuable test system as an alternative or replacement to live human or animal testing for absorption, toxicity, and in many cases effectiveness of products. The production of the matrix has been shown to mimic several of the processes exhibited in production of matrix as well as repair of matrix in vivo. Because of this, the system described can be a valuable tool in the analysis of wound repair and tissue generation and further for the testing and analysis of chemical and/or physical stimulants of wound repair.

The most preferred use for the skin constructs of this invention is for grafting or implantation in a mammalian host to restore or repair the skin due to injury or disease. Indications for grafting of a skin construct include but are not limited to plastic or reconstructive surgery, skin wounds, burns, psoriasis, venous and diabetic ulcers, and basal cell carcinoma. Skin constructs of the invention are useful to both protect the wounded tissue, and then serve as a scaffold for the ingrowth of the host tissue. It is believed that the level of organization of the tissue produced in this invention would also serve to ease and possibly speed up the actions of wound repair.

The cell matrix constructs of the invention have cohesive properties. "Cohesive" as used herein, means being able to maintain physical unitary integrity and tissue-like handing properties. The physical properties that primarily give the constructs of the invention cohesive properties are bulk thickness and fibrous matrix structure. The fibrous extracellular matrix is formed from cell-synthesized collagen and other matrix components, mainly fibrillar collagen arranged in fibrils and fibril bundles, and gives the constructs their bulk. The cell-matrix constructs of the invention are handleable, that is, they can be manually peeled from their culture substrate, without a carrier support or specialized tools, and applied to the patient or to a testing apparatus. It can withstand damage such as tearing or stretching from ordinary manipulation in the clinic without detriment to the structure or function. When applied to a patient, they can be secured in place by sutures or staples.

To graft the skin construct of the present invention to a patient, the graft area is prepared according to standard practice. For burn indications, the burned wound sites to be grafted are to be prepared for the graft so that the burned skin area is completely excised. Excised beds will appear clean and clinically uninfected prior to grafting. For deep partial thickness wounds due to surgical excision, the pre-operative area is shaved, if necessary, cleansed with an antimicrobial antiseptic skin cleanser and rinsed with normal saline. Local anesthesia usually consists of intradermal administration of lidocaine or epinephrine or both. Once anesthesia is accomplished, a dermatome is used to remove skin to an appropriate depth, creating a deep partial thickness wound. Hemostasis can be achieved by compression with epinephrine containing lidocaine and by electrocautery. The skin construct is then applied to the wound bed and, if necessary, is secured by suturing or stapling in place, then bolstered and bandaged with appropriate dressings.

The skin construct of the present invention may also be meshed prior grafting to a patient. Meshing improves conformation of the skin construct to the wound bed and provides a means for draining wound exudate from beneath the graft. The term 'meshing' is defined as a mechanical method by which a tissue is perforated with slits to form a net-like arrangement. Meshing is preferably obtained by the use of a conventional skin mesher (ZIMMER®; BIOPLASTY®). One could also manually score or perforate a tissue with a scalpel or a needle. Meshed skin may be expanded by stretching the skin so that the slits are opened and then applied to the wound bed. Expanded meshed tissue provides a wound area with maximal coverage. Alternatively, meshed skin may be applied without expansion, simply as a sheet with an arrangement of unexpanded slits. The meshed skin construct may be applied alone or with the patient's own skin from another area of the body. Tissue constructs may also have perforations or fenestrations and pores provided by other means. Fenestrations may be applied manually using a laser, punch, scalpel, needle or pin.

The skin construct of the invention may be applied to wounds other than surgical wounds or burn areas. Other wounds such as venous ulcers, diabetic ulcers, decubitus ulcers may experience a healing benefit by application of the disclosed skin construct. Other congenital skin diseases such as epidermolysis bullosa may benefit as well.

The following examples are provided to better explain the practice of the present invention and should not be interpreted in any way to limit the scope of the present invention. Those skilled in the art will recognize that various modifications can be made to the methods described herein while not departing from the spirit and scope of the present invention.

EXAMPLES

Example 1

Formation of a Collagenous Matrix by Human Neonatal Foreskin Fibroblasts

Human neonatal foreskin fibroblasts (originated at Organogenesis, Inc. Canton, Mass.) were seeded at $5\times10^5$ cells/ 162 cm$^2$ tissue culture treated flask (Costar Corp., Cambridge, Mass., cat #3150) and grown in growth medium. The growth medium consisted of: Dulbecco's Modified Eagle's medium (DMEM) (high glucose formulation, without L-glutamine, BioWhittaker, Walkersville, Md.) supplemented with 10% newborn calf serum (NBCS) (HyClone Laboratories, Inc., Logan, Utah) and 4 mM L-glutamine (BioWhittaker, Walkersville, Md.). The cells were maintained in an incubator at 37±1° C. with an atmosphere of 10±1% $CO_2$. The medium was replaced with freshly prepared medium every two to three days. After 8 days in culture, the cells had grown to confluence, that is, the cells had formed a packed monolayer along the bottom of the tissue culture flask, and the medium was aspirated from the culture flask. To rinse the monolayer, sterile-filtered phosphate buffered saline was added to the bottom of each culture flask and then aspirated from the flasks. Cells were released from the flask by adding 5 mL trypsin-versene glutamine (BioWhittaker, Walkersville, Md.) to each flask and gently rocking to ensure complete coverage of the monolayer. Cultures were returned to the incubator. As soon as the cells were released 5 ml of SBTI (Soybean Trypsin Inhibitor) was added to each flask and mixed with the suspension to stop the action of the trypsin-versene. The cell suspension was removed from the flasks and evenly divided between sterile, conical centrifuge tubes. Cells were collected by centrifugation at approximately 800-1000×g for 5 minutes.

Cells were resuspended using fresh medium to a concentration of $3.0\times10^6$ cells/ml, and seeded onto 0.4 micron pore size, 24 mm diameter tissue culture treated inserts (TRANSWELL®, Corning Costar) in a six-well tray at a density of $3.0\times10^6$ cells/insert ($6.6\times10^5$ cells/cm$^2$). The cells were maintained in an incubator at 37±1° C. with an atmosphere of 10±1% $CO_2$ and fed fresh production medium every 2 to 3 days for 21 days. The production medium comprised: a 3:1 base mixture of DMEM and Hams F-12 medium (Quality Biologics Gaithersburg, Md.), 4 mM GlutaMAX-1™ (Gibco BRL, Grand Island, N.Y.) and additives to a resultant concentration of: 5 ng/ml human recombinant epidermal growth factor (Upstate Biotechnology Lake Placid, N.Y.), 2% newborn calf serum (Hyclone, Logan, Utah), 0.4 µg/ml hydrocortisone (Sigma St. Louis, Mo.), $1\times10^{-4}$ M ethanolamine (Fluka, Ronkonkoma, N.Y. ACS grade), $1\times10^{-4}$ M o-phosphoryl-ethanolamine (Sigma, St. Louis), 5 µg/ml insulin (Sigma, St. Louis, Mo.), 5 µg/ml transferrin (Sigma, St. Louis, Mo.), 20 pM triiodothyronine (Sigma, St. Louis, Mo.), and 6.78 ng/ml selenium (Sigma Aldrich Fine Chemicals Co., Milwaukee, Wis., 50 ng/ml L-ascorbic acid (WAKO Chemicals USA, Inc. #013-12061), 0.2 µg/ml L-proline (Sigma, St. Louis, Mo.), 0.1 µg/ml glycine (Sigma, St. Louis, Mo.) and 0.05% poly-ethylene glycol (PEG) 3400-3700 MW (cell culture grade) (Sigma, St. Louis, Mo.).

Samples for histological analysis were taken at days 7, 14 and 21 and fixed in formalin, then embedded in paraffin. The formalin fixed samples were embedded in paraffin and 5 micrometer section were stained with hematoxylin-eosin (H&E) according to procedures known in the art. Using H&E stained slides, thickness measurements were made to ten randomly picked microscopic fields utilizing a 10× eyepiece loaded with a 10 mm/100 micrometer reticle.

Results for two different cell strains of human dermal fibroblasts are summarized in Table 1, which shows the thickness of the cell-matrix construct as it develops.

TABLE 1

| | Thickness (microns) | | | |
| --- | --- | --- | --- | --- |
| | Day 0 | Day 7 | Day 14 | Day 21 |
| B119 Average (n = 3) | 0 | 30.33 ± 2.61 | 63.33 ± 4.40 | 84.00 ± 4.67 |
| B156 Average (n = 4) | 0 | 42.00 ± 5.14 | 63.85 ± 4.50 | 76.25 ± 8.84 |

Samples were also submitted for collagen concentration analysis on days 7, 14, and 21. Collagen content was estimated by employing a calorimetric assay for hydroxyproline content known in the art (Woessner, 1961). At those same timepoints cell number was also determined. Table 2 is a summary of collagen concentration and Table 3 is a summary of the cell data from cell-matrix constructs produced from two different cell strains (B156 and B119) using the procedure described above.

TABLE 2

| | Collagen ($\mu g/cm^2$) | | | |
| --- | --- | --- | --- | --- |
| | Day 0 | Day 7 | Day 14 | Day 21 |
| B119 Average (n = 3) | 0 | 93.69 ± 22.73 | 241.66 ± 21.08 | 396.30 ± 29.38 |
| B156 Average (n = 3) | 0 | 107.14 ± 17.16 | 301.93 ± 23.91 | 457.51 ± 25.00 |

TABLE 3

| | Cells ($cells/cm^2$) | | | |
| --- | --- | --- | --- | --- |
| | Day 0 | Day 7 | Day 14 | Day 21 |
| B119 Average (n = 3) | $6.6 \times 10^5$ | $11.8 \pm 4.4 \times 10^5$ | $11.4 \pm 1.7 \times 10^5$ | $13.9 \pm 1.2 \times 10^5$ |
| B156 Average (n = 3) | $6.6 \times 10^5$ | $13.1 \pm 0.5 \times 10^5$ | $14.0 \pm 2.1 \times 10^5$ | $17.1 \pm 1.7 \times 10^5$ |

Samples of the human cell derived dermal matrix from days 7, 14, and 21 were analyzed by delayed reduction SDS-PAGE to determine collagen composition revealing type I and type III collagen alpha bands in the samples.

Biochemical characteristics of the dermal matrix were determined using immunohistochemical methods. Fibronectin identification was carried out on paraffin fixed sections using the Zymed Histostain strepavidin-biotin system (Zymed Laboratories Inc., South San Francisco, Calif.). Tenascin presence was determined by primary anti-tenascin antibody staining (Dako, Carpintheria, Calif.) followed by anti-mouse horseradish peroxidase labeled antibody (Calbiochem) as a secondary antibody. Samples were visualized by applying diaminobenzyne (Sigma St. Louis, Mo.) and counterstained with Nuclear Fast red.

Glycosaminoglycan (GAG) quantification was performed on 21 day samples using the previously described method (Farndale, 1986). The assay showed the presence of 0.44 grams of GAG per $cm^2$ in a sample of human cell derived dermal matrix taken 21 days post seeding.

Example 2

Full Thickness Skin Construct

Using a dermal construct formed using the method described in Example 1, normal human neonatal foreskin epidermal keratinocytes (originated at Organogenesis, Inc. Canton, Mass.) were plated onto the cell-matrix construct to form the epidermal layer of the skin construct.

The medium was aseptically removed from the culture insert and its surrounds. Normal human epidermal keratinocytes were scaled up to passage 4 from frozen subculture cell stock to confluence. Cells were then released from the culture dishes using trypsin-versene, pooled, centrifuged to form a cell pellet, resuspended in epidermalization medium, counted and seeded on top of the membrane at a density of $4.5 \times 10^4$ cells/$cm^2$. The constructs are then incubated for 90 minutes at 37±1° C., 10% $CO_2$ to allow the keratinocytes to attach. After the incubation, the constructs were submerged in epidermalization medium. The epidermalization medium is composed of: a 3:1 base mixture of Dulbecco's Modified Eagle's Medium (DMEM) (high glucose formulation, without L-glutamine (BioWhittaker, Walkersville, Md.) and Hams F-12 medium (Quality Biologics Gaithersburg, Md.), supplemented with 0.4 µg/ml hydrocortisone (Sigma St. Louis, Mo.), $1 \times 10^{-4}$ M ethanolamine (Fluka, Ronkonkoma, N.Y.), $1 \times 10^{-4}$ M O-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 pM triiodothyronine (Sigma, St. Louis, Mo.), 6.78 ng/ml selenium (Aldrich), 24.4 µg/ml adenine (Sigma Aldrich Fine Chemicals Company, Milwaukee, Wis.), 4 mM L-glutamine (BioWhittaker, Walkersville, Md.), 0.3% chelated new born calf serum (Hyclone, Logan, Utah), 0.628 ng/ml progesterone (Amersham Arlington Heights, Ill.), 50 µg/ml L-ascorbate sodium salt (Sigma Aldrich Fine Chemicals Company, Milwaukee, Wis.), 10 ng/ml epidermal growth factor (Life Technologies Inc., Md.), and 50 µg/ml gentamycin sulfate (Amersham, Arlington Heights, Ill.). The constructs were cultured in the epidermalization medium for 2 days at 37±1° C., 10% $CO_2$.

After 2 days the construct was submerged in media composed of; 3:1 mixture of Dulbecco's modified Eagle's medium (DMEM) (high glucose formulation, without L-glutamine, BioWhittaker, Walkersville, Md.), Hams F-12 medium (Quality Biologics, Gaithersburg, Md.), supplemented with 0.4 µg/ml hydrocortisone (Sigma, St. Louis, Mo.), $1 \times 10^{-4}$ ethanolamine (Fluka, Ronkonkoma, N.Y.), $1 \times 10^{-4}$ o-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 pM triiodothyronine (Sigma, St. Louis, Mo.), and 6.78 ng/ml selenium (Sigma Aldrich Fine Chemicals Company, Milwaukee, Wis.), 24.4 µg/ml adenine (Sigma Aldrich Fine Chemicals Company), 4 mM L-glutamine (BioWhittaker, Walkersville, Md.), 0.3% chelated new born calf serum (BioWhittaker, Walkersville, Md.), 0.628 ng/ml progesterone (Amersham, Arlington Heights, Ill.), 50 µg/ml sodium ascorbate, 265 µg/ml calcium chloride (Mallinckrodt, Chesterfield, Mo.), and 50 µg/ml gentamycin sulfate (Amersham, Arlington Heights, Ill.). Again the construct was incubated at 37±1° C., 10% $CO_2$ for 2 days.

After the 2 days the carrier containing the construct was aseptically transferred to new culturing trays with a sufficient amount cornification media, 9 mL, to achieve a fluid level just to the surface of the carrier membrane to maintain a dry interface to allow stratification of the epithelial layer. The constructs were incubated at 37±1° C., 10% $CO_2$, and low humidity, in media with media changes every 2-3 days for 7 days. This medium is composed of; a 1:1 mixture of Dulbecco's modified Eagle's medium (DMEM) (high glucose formulation, without L-glutamine BioWhittaker, Walkersville, Md.), Hams F-12 medium (Quality Biologics, Gaithersburg, Md.), supplemented with 0.4 µg/ml hydrocortisone (Sigma, St. Louis, Mo.), $1\times10^{-4}$ M ethanolamine (Fluka, Ronkonkoma, N.Y.), $1\times10^{-4}$ M o-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 pM triiodothyronine (Sigma, St. Louis, Mo.), 6.78 µg/ml selenium (Aldrich), 24.4 µg/ml adenine (Sigma Aldrich Fine Chemicals Company), 4 mM L-glutamine (BioWhittaker, Walkersville, Md.), 2% new born calf serum (BioWhittaker, Walkersville, Md.), 50 µg/ml sodium ascorbate, and 50 µg/ml gentamycin sulfate (Amersham, Arlington Heights, Ill.). After 7 days the construct was fed for 10 more days, with changes every 2-3 days with a maintenance medium. This maintenance medium was composed of; 1:1 mixture of Dulbecco's modified Eagle's medium (DMEM) (high glucose formulation, without L-glutamine, BioWhittaker, Walkersville, Md.), Hams F-12 medium (Quality Biologics Gaithersburg, Md.), 0.4 µg/ml hydrocortisone (Sigma St. Louis, Mo.), $1\times10^{-4}$ M ethanolamine (Fluka, Ronkonkoma, N.Y.), $1\times10^{-4}$ M o-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 pM triiodothyronine (Sigma, St. Louis, Mo.), and 6.78 ng/ml selenium (Sigma Aldrich Fine Chemicals Company, Milwaukee, Wis.), 24.4 µg/ml adenine (Sigma Aldrich Fine Chemicals Company, Milwaukee, Wis.), 4 mM L-glutamine (BioWhittaker, Walkersville, Md.), 1% new born calf serum (BioWhittaker, Walkersville, Md.), and 50 µg/ml gentamycin sulfate (Amersham, Arlington Heights, Ill.).

Final samples were submitted for hemotoxylin and eosin processing as described in Example 1 to determine gross appearance under light microscopy. The resulting construct consisted of a lower (dermal) layer consisting of fibroblasts surrounded by matrix having features described in Example 1, and was completely overlaid by a multilayered, stratified and well-differentiated layer of keratinocytes that exhibit a basal layer, a suprabasal layer, a granular layer and a stratum corneum similar to that of skin in situ. The skin construct has a well-developed basement membrane present at the dermal-epidermal junction as exhibited by transmission electron microscopy (TEM). The basement membrane appears thickest around hemidesmosomes, marked by anchoring fibrils that are comprised of type VII collagen, as visualized by TEM. As expected these anchoring fibrils can easily be seen exiting from the basement membrane and entrapping the collagen fibrils. The presence of laminin, a basement membrane glycoprotein, was shown using the previously described avidin-biotin immunoenzymatic technique (Guesdon, 1979).

Example 3

In Vitro Formation of a Collagenous Matrix by Human Neonatal Foreskin Fibroblasts in Chemically Defined Medium Human neonatal foreskin fibroblasts were expanded using the procedure described in Example 1. Cells were then resuspended to a concentration of $3\times10^6$ cells/ml and seeded on to 0.4 micron pore size, 24 mm diameter tissue culture treated membrane inserts in a six-well tray at a density of $3.0\times10^6$ cells/TW ($6.6\times10^5$ cells/cm$^2$). These cells were then maintained as Example 1 with newborn calf serum omitted from the media throughout. More specifically the medium contained: a base 3:1 mixture of DMEM, Hams F-12 medium (Quality Biologics, Gaithersburg, Md.), 4 mM GlutaMAX (Gibco BRL, Grand Island, N.Y.) and additives: 5 ng/ml human recombinant epidermal growth factor (Upstate Biotechnology, Lake Placid, N.Y.), 0.4 µg/ml hydrocortisone (Sigma, St. Louis, Mo.), $1\times10^{-4}$ M ethanolamine (Fluka, Ronkonkoma, N.Y. cat. #02400 ACS grade), $1\times10^{-4}$ M o-phosphoryl-ethanolamine (Sigma, St Louis, Mo.), 5 µg/ml insulin (Sigma, St. Louis, Mo.), 5 µg/ml transferrin (Sigma, St. Louis, Mo.), 20 pM triiodothyronine (Sigma, St. Louis, Mo.), and 6.78 ng/ml selenium (Sigma Aldrich Fine Chemicals Company, Milwaukee, Wis.), 50 ng/ml L-ascorbic acid (WAKO Chemicals USA, Inc.), 0.2 µg/ml L-proline (Sigma, St. Louis, Mo.), 0.1 µg/ml glycine (Sigma, St. Louis, Mo.) and 0.05% poly-ethylene glycol (PEG) (Sigma, St. Louis, Mo.). Samples were checked at day 7, 14, and 21 for collagen concentration and cell number using described procedures. Results are summarized in tables 4 (cell number) and 5 (collagen). Samples were also formalin fixed and processed for hemotoxylin and eosin staining for light microscope analysis as described in Example 1. Histological evaluation demonstrated that the constructs grown in defined medium was similar to those grown in the presence of 2% newborn calf serum. Samples also stained positively for fibronectin, using procedure described in Example 1.

TABLE 4

| | Collagen (µg/cm$^2$) | | | |
| --- | --- | --- | --- | --- |
| | Day 0 | Day 7 | Day 14 | Day 21 |
| Average amount of collagen in each construct (n = 3) | 0 | 107.63 ± 21.96 | 329.85 ± 27.63 | 465.83 ± 49.46 |

TABLE 5

| | Cells (cells/cm$^2$) | | | |
| --- | --- | --- | --- | --- |
| | Day 0 | Day 7 | Day 14 | Day 21 |
| Average number of cells in each construct (n = 3) | $6.6\times10^5$ | $7.8 \pm 2.2 \times 10^5$ | $9.6 \pm 2.5 \times 10^5$ | $1.19 \pm 2.1 \times 10^5$ |

Besides endogenously produced fibrillar collagen, decorin and glycosaminoglycan were also present in the cell-matrix construct.

Example 4

Full Thickness Skin Construct Formed Using Chemically Defined Media

Using a 25 day dermal construct formed by human dermal fibroblasts under chemically defined conditions similar to the method described in Example 3, normal human neonatal foreskin epidermal keratinocytes were seeded on the top surface of the cell-matrix construct to form the epidermal layer of the skin construct.

The medium was aseptically removed from the culture insert and its surrounds. Normal human epidermal keratinocytes were scaled up to passage 4 from frozen subculture cell stock to confluence. Cells were then released from the culture dishes using trypsin-versene, pooled, centrifuged to form a cell pellet, resuspended in epidermalization medium, counted and seeded on top of the membrane at a density of $4.5 \times 10^4$ cells/cm$^2$. The constructs were then incubated for 90 minutes at 37±1° C., 10% $CO_2$ to allow the keratinocytes to attach. After the incubation, the constructs were submerged in epidermalization medium. The epidermalization medium is composed of: a 3:1 base mixture of Dulbecco's Modified Eagle's Medium (DMEM) (containing no glucose and no calcium, BioWhittaker, Walkersville, Md.) and Hams F-12 medium (Quality Biologics Gaithersburg, Md.), supplemented with 0.4 µg/ml hydrocortisone (Sigma St. Louis, Mo.), $1 \times 10^{-4}$ M ethanolamine (Fluka, Ronkonkoma, N.Y.), $1 \times 10^{-4}$ M o-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 pM triiodothyronine (Sigma, St. Louis, Mo.), 6.78 µg/ml selenium (Aldrich), 24.4 µg/ml adenine (Sigma Aldrich Fine Chemicals Company, Milwaukee, Wis.), 4 mM L-glutamine (BioWhittaker, Walkersville, Md.), 50 µg/ml L-ascorbate sodium salt (Sigma Aldrich Fine Chemicals Company, Milwaukee, Wis.), 16 µM linoleic acid (Sigma, St. Louis, Mo.), 1 µM tocopherol Acetate (Sigma, St. Louis, Mo.) and 50 µg/ml gentamicin sulfate (Amersham, Arlington Heights, Ill.). The constructs were cultured in the epidermalization medium for 2 days at 37±1° C., 10±1% $CO_2$.

After 2 days the medium was exchanged with fresh medium composed as above, and returned to the incubator set at 37±1° C., 10±1% $CO_2$ for 2 days. After the 2 days, the carrier containing the construct was aseptically transferred to new culturing trays with sufficient media to achieve a fluid level just to the surface of the carrier membrane to maintain the developing construct at the air-liquid interface. The air contacting the top surface of the forming epidermal layer allows stratification of the epithelial layer. The constructs were incubated at 37±1° C., 10% $CO_2$, and low humidity, in media with media changes every 2-3 days for 7 days. This medium contained a 1:1 mixture of Dulbecco's modified Eagle's medium (DMEM) (containing no glucose and no calcium, BioWhittaker, Walkersville, Md.), Hams F-12 medium (Quality Biologics, Gaithersburg, Md.), supplemented with 0.4 µg/ml hydrocortisone (Sigma, St. Louis, Mo.), $5 \times 10^{-4}$ M ethanolamine (Fluka, Ronkonkoma, N.Y.), $5 \times 10^{-4}$ M o-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 pM triiodothyronine (Sigma, St. Louis, Mo.), 6.78 ng/ml selenium (Sigma Aldrich Fine Chemicals Company), 24.4 µg/ml adenine (Sigma Aldrich Fine Chemicals Company), 4 mM L-glutamine (BioWhittaker, Walkersville, Md.), 2.65 µg/ml calcium chloride (Mallinckrodt, Chesterfield, Mo.), 16 µM linoleic acid (Sigma, St. Louis, Mo.), 1 µM tocopherol acetate (Sigma, St. Louis, Mo.), 1.25 mM serine (Sigma, St. Louis, Mo.), 0.64 mM choline chloride (Sigma, St. Louis, Mo.) and 50 µg/ml gentamicin sulfate (Amersham, Arlington Heights, Ill.). The cultures were fed every 2-3 days, for 14 days.

Samples, in triplicate, were submitted 10, 12, and 14 days after the construct was lifted to the air-liquid interface for hematoxylin and eosin processing as described in Example 1 to determine gross appearance under light microscopy. The resulting construct consisted of a lower (dermal) layer consisting of fibroblasts surrounded by matrix having features as described in Example 3, and was overlaid by a layer of stratified and differentiated keratinocytes.

Example 5

In Vitro Formation of a Collagenous Matrix by Human Achilles Tendon Fibroblasts

Cell-matrix constructs were formed using the same method described in Example 1 replacing the human neonatal foreskin fibroblasts with human Achilles tendon fibroblasts (HATF). Following 21 days in production medium, samples were also submitted for H&E staining and thickness determination using the procedure described in Example 1. The resulting construct was visualized as a cell matrix tissue like construct with a thickness of 75.00±27.58 microns (n=2). Endogenously produced fibrillar collagen, decorin and glycosaminoglycan were also present in the construct.

Example 6

In Vitro Formation of a Collagenous Matrix by Transfected Human Neonatal Foreskin Fibroblasts Transfected human dermal fibroblasts were produced using the following procedure. One vial of jCRIP-43 platelet derived growth factor (PDGF) viral producers (Morgan, J., et al.) was thawed, and the cells were seeded at $2 \times 10^6$ cells/162 cm$^2$ flask (Corning Costar, Cambridge, Mass.). These flasks were fed a growth medium, and maintained in an incubator at 37±1° C. with an atmosphere of 10±1% $CO_2$. The growth medium consisted of: Dulbecco's modified Eagle's medium (DMEM) (high glucose formulation, without L-glutamine, BioWhittaker, Walkersville, Md.) supplemented with 10% newborn calf serum (HyClone Laboratories, Inc., Logan, Utah) and 4 mM L-glutamine (BioWhittaker, Walkersville, Md.). On the same day, 1 vial of human neonatal foreskin fibroblast (HDFB156) was also thawed and plated at $1.5 \times 10^6$ cells/162 cm$^2$ flask (Corning Costar, Cambridge, Mass.). After three days the jCRIP PDGF-43 viral producers were fed with fresh growth medium. The HDFB156 were fed with the above growth medium plus 8 µg/ml polybrene (Sigma, St. Louis, Mo.). The next day the HDFB156's cells were infected as follows. The spent medium from the jCRIP PDGF-43 viral producers was collected and filtered through a 0.45 micron filter. 8 µg/ml polybrene was added to this filtered spent medium. The spent medium was then placed on the HDF. On the next two days the HDF were fed fresh growth medium. The day after the HDF were passed from p5 to p6 and seeded at a density of $2.5 \times 10^6$ cells/162 cm$^2$ flask (Corning Costar, Cambridge, Mass.). Cells were passed as follows; spent medium was aspirated off. The flasks were then rinsed with a phosphate buffered saline to remove any residual newborn calf serum. Cells were released from the flask by adding 5 mL trypsin-versene to each flask and gently rocking to ensure complete coverage of the monolayer. Cultures were returned to the incubator. As soon as the cells were released, 5 mL of SBTI (Soybean Trypsin Inhibitor) was added to each flask and mixed with the suspension to stop the action of the trypsin-versene. The cell/Trypsin/SBTI suspension was removed from the flasks and evenly divided between sterile, conical centrifuge tubes. Cells were collected by centrifugation at approximately 800-1000×g for 5 minutes). The cells were resuspended in the growth media for seeding at the density listed above. After two days the cells were fed fresh growth medium. The following day the cells were harvested as above, and diluted to a density of $1.5\times10^6$ cells/ml in growth medium containing 10% newborn calf serum (NBCS) with 10% dimethyl sulfoxide (DMSO) (Sigma, St. Louis, Mo.). The cells were then frozen 1 ml/cryovial at about $-80°$ C.

Production of the collagenous matrix for this example utilize the same procedure as Examples 1 and 3, replacing the human neonatal foreskin fibroblasts with human neonatal foreskin fibroblasts transformed to produce high levels of platelet derived growth factor (PDGF) as described above. Samples were taken for H&E staining as described above on day 18 post seeding. Samples were also stained using the avidin-biotin methods for the presence of fibronectin listed in Example 10. Samples were taken on day 18 post seeding for H&E staining as described in Example 1, and exhibited a similar cell-matrix gross appearance to that described in Example 1, with a measured thickness of 123.6 microns (N=1). PDGF output of the transfected cells in the cell-matrix construct was measured to be 100 ng/mL by ELISA throughout the duration of the culture (18 days) while control output of PDGF was undetectable.

Example 7

Use of the Dermal Construct as a Graft Material

Cell-matrix constructs were prepared according to the methods in Example 1 using human dermal fibroblasts derived from neonate foreskin and were grafted onto full excision wounds created on nude athymic mice. Mice were grafted according to the methods described by Parenteau, et al. (1996), the disclosure of which is incorporated herein. Grafts were examined at 14, 28 and 56 days for signs of adherence to the wound bed, evidence of wound contraction, areas of graft loss, and presence of vascularization (color). The graft areas were photographed while intact on the mice. A number of mice were sacrificed at each timepoint, and the graft areas and their surrounds were excised along with a surrounding rim of murine skin to at least the panniculus carnosus. Junctions between the graft and the murine skin were preserved in each sample. The explanted tissue samples were then fixed in phosphate buffered 10% formalin and fixation in methanol. Formalin fixed samples were processed for H&E staining according to procedure described in Example 1. Grafts were able to integrate with the mouse skin, with minimal contraction noted. Within 14 days of grafting, the mouse epidermis had migrated completely over the graft. Using the H&E stained samples, vessels were obvious within the graft at 14 days, and throughout the experiment. By gross observation and by H&E stained samples, it was determined that the graft persisted and remained healthy looking (contained living cells, no gross matrix abnormalities, etc.) throughout the length of the experiment.

Example 8

Use of Full Thickness Skin Construct as a Skin Graft

Bilayer skin constructs were prepared as described in Example 2 using human dermal fibroblasts derived from neonate foreskin in the dermal layer and human keratinocytes derived from a different neonate foreskin in the epidermal layer. The skin constructs were able to be manually peeled from the membrane, handled without carrier support, and placed onto the graft site. The bilayer skin constructs were grafted onto full excision wounds created on athymic nude mice according to the methods described by Parenteau, et al. (1996), the disclosure of which is incorporated herein. Timepoints for taking samples were days 7, 14, 28, 56, and 184 days post-graft graft. The graft areas were photographed while intact on the mice. A number of mice were sacrificed at each timepoint, and the graft areas and their surrounds were excised along with a surrounding rim of murine skin to at least the panniculus carnosus. Junctions between the graft and the murine skin were preserved in each sample. The explanted tissue samples were then fixed in phosphate buffered 10% formalin and fixation in methanol. Formalin fixed samples were processed for H&E staining according to procedure described in Example 1.

The grafts integrated with the host tissue within 7 days by gross observation as well as by histological appearance. By H&E staining, vessels were visualized growing into the graft from the host tissue within 7 days of grafting. The grafts remained healthy and persisted through the experiment, with minimal contraction noted. Utilizing anti-human Involucrin staining the persistence of human epidermal cells was shown for the entire graft period.

Example 9

In Vitro Formation of a Matrix by Human Corneal Keratocytes

Human corneal keratocyte cells (originated at Organogenesis, Inc. Canton, Mass.) were used in the production of a stromal construct of cornea. Confluent cultures of human keratocytes were released from their culture substrates using trypsin-versene. When released, soybean trypsin inhibitor was used to neutralize the trypsin-versene, the cell suspension was centrifuged, the supernatant discarded and the cells were then resuspended in base media to a concentration of $3\times10^6$ cells/ml. Cells were seeded onto 0.4 micron pore size, 24 mm diameter tissue culture treated transwells in a six-well tray at a density of $3.0\times10^6$ cells/TW ($6.6\times10^5$ cells/cm$^2$). These cultures were maintained overnight in seed medium. The seed medium was composed of: a base 3:1 mixture of Dulbecco's Modified Eagle's Medium (DMEM) and Hams F-12 Medium (Quality Biologics Gaithersburg, Md. cat.), 4 mM GlutaMAX (Gibco BRL, Grand Island, N.Y.) and additives: 5 ng/ml human recombinant epidermal growth factor (EGF) (Upstate Biotechnology Lake Placid, N.Y.), 0.4 µg/ml hydrocortisone (Sigma St. Louis, Mo.), $1\times10^{-4}$ M ethanolamine (Fluka, Ronkonkoma, N.Y.), $1\times10^{-4}$ M o-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 pM triiodothyronine (Sigma, St. Louis, Mo.), and 6.78 ng/ml selenium (Sigma Aldrich Fine Chemicals Company, Milwaukee, Wis.). Following this the cultures were fed fresh production medium. The production medium was composed of: a base 3:1 mixture of DMEM, Hams F-12 medium (Quality Biologics Gaithersburg, Md.), 4 mM GlutaMAX (Gibco BRL., Grand Island, N.Y.) and additives: 5 ng/ml Human Recombinant Epidermal growth factor (Upstate Biotechnology Lake Placid, N.Y.), 2% newborn calf serum (Hyclone, Logan, Utah), 0.4 µg/ml hydrocortisone (Sigma, St. Louis, Mo.), $1\times10^{-4}$ M ethanolamine (Fluka, Ronkonkoma, N.Y. ACS grade), $1\times10^{-4}$ M o-phosphoryl-ethanolamine (Sigma, St. Louis), 5 µg/ml insulin (Sigma, St. Louis, Mo.), 5 µg/ml transferrin (Sigma, St. Louis, Mo.), 20 pM triiodothyronine (Sigma, St. Louis, Mo.), and 6.78 ng/ml selenium (Sigma Aldrich Fine Chemicals Co., Milwaukee, Wis.), 50 ng/ml L-ascorbic acid (WAKO pure chemical company), 0.2 µg/ml L-proline (Sigma, St. Louis, Mo.), 0.1 µg/ml glycine (Sigma, St. Louis, Mo.) and 0.05% poly-ethylene glycol (PEG) (Sigma, St. Louis, Mo., cell culture grade).

The cells were maintained in an incubator at 37±1° C. with an atmosphere of 10%±1% $CO_2$ and fed fresh production medium every 2-3 days for 20 days (for a total of 21 days in culture. After 21 days in culture, the keratocytes had deposited a matrix layer of about 40 microns in thickness, as measured by the method described in Example 1. Endogenously produced fibrillar collagen, decorin and glycosaminoglycan were also present in the cell-matrix construct.

Example 10

In Vitro Formation of a Collagenous Matrix by Human Neonatal Foreskin Fibroblasts Seeded in Production Media Human neonatal foreskin fibroblasts (originated at Organogenesis, Inc. Canton, Mass.) were seeded at $1\times10^5$ cells/0.4 micron pore size, 24 mm diameter tissue culture treated carriers in a six-well tray (TRANSWELL®, Costar Corp. Cambridge, Mass.) and grown in growth medium. The growth medium consisted of: Dulbecco's Modified Eagle's medium (DMEM) (high glucose formulation, without L-glutamine, BioWhittaker, Walkersvile, Md.) supplemented with 10% newborn calf serum (HyClone Laboratories, Inc., Logan, Utah) and 4 mM L-Glutamine (BioWhittaker, Walkersville, Md.). The cells were maintained in an incubator at 37±1° C. with an atmosphere of 10±1% $CO_2$. The medium was replaced every two to three days. After 9 days in culture the medium was aspirated from the culture dish, and replaced with production medium. The cells were maintained in an incubator at 37±1° C. with an atmosphere of 10±1% $CO_2$ and fed fresh production medium every 2-3 days for 21 days. The production medium was composed of: a base 3:1 mixture of DMEM, Hams F-12 medium (Quality Biologics, Gaithersburg, Md.), 4 mM GlutaMAX (Gibco BRL, Grand Island, N.Y.) and additives: 5 ng/ml human recombinant epidermal growth factor (Upstate Biotechnology, Lake Placid, N.Y.), 2% newborn calf serum (Hyclone, Logan, Utah), 0.4 µg/ml hydrocortisone (Sigma St. Louis, Mo.), $1\times10^{-4}$ M ethanolamine (Fluka, Ronkonkoma, N.Y. ACS grade), $1\times10^{-4}$ M o-phosphoryl-ethanolamine (Sigma, St. Louis), 5 µg/ml insulin (Sigma, St. Louis, Mo.), 5 µg/ml transferrin (Sigma, St. Louis, Mo.), 20 pM triiodothyronine (Sigma, St. Louis, Mo.), and 6.78 ng/ml selenium (Sigma Aldrich Fine Chemicals Co., Milwaukee, Wis.), 50 ng/ml L-ascorbic acid (WAKO Pure Chemical Company), 0.2 µg/ml L-proline (Sigma, St. Louis, Mo.), 0.1 µg/ml glycine (Sigma, St. Louis, Mo.) and 0.05% poly-ethylene glycol (PEG) (Sigma, St. Louis, Mo., cell culture grade).

Samples were taken at day 21 and fixed in formalin, then embedded in paraffin. The formalin fixed samples were embedded in paraffin and 5 micrometer section were stained with hematoxylin-eosin (H&E) according techniques routinely used in the art. Using H&E stained slides, measurements were made at ten randomly picked microscopic fields utilizing a 10× Eyepiece (Olympus America Inc., Melville, N.Y.) loaded with a 10 mm/100 micrometer reticle (Olympus America Inc., Melville, N.Y.). The constructs created using this method are similar in structure and biochemical composition to those created with Example 1, and have a measured thickness of 82.00±7.64 microns.

Example 11

In Vitro Formation of a Collagenous Matrix by Pig Dermal Fibroblasts

Pig Dermal Fibroblasts (originated at Organogenesis, Inc. Canton, Mass.) were seeded at $5\times10^5$ cells/162 $cm^2$ tissue culture treated flask (Costar Corp., Cambridge, Mass. cat #3150) and grown in growth medium as described below. The growth medium consisted of; Dulbecco's modified Eagle's medium (DMEM) (high glucose formulation, without L-glutamine, BioWhittaker, Walkersville, Md.) supplemented with 10% fetal calf serum (HyClone Laboratories, Inc., Logan, Utah) and 4 mM L-glutamine (BioWhittaker, Walkersville, Md.). The cells were maintained in an incubator at 37±1° C. with an atmosphere of 10%±1% $CO_2$. The medium was replaced every two to three days. Upon confluence, that is the cells had formed a packed layer at the bottom of the tissue culture flask, the medium was aspirated from the culture dish. To rinse the monolayer, sterile-filtered phosphate buffered saline was added to the monolayer and then aspirated from the dish. Cells were released from the flask by adding 5 ml trypsin-versene glutamine (BioWhittaker, Walkersville, Md.) to each flask and gently rocking to ensure complete coverage of the monolayer. Cultures were returned to the incubator. As soon as the cells were released 5 ml of SBTI (Soybean Trypsin Inhibitor) was added to each flask and mixed with the cell suspension to stop the action of the trypsin-versene. The suspension was removed from the flasks and evenly divided between sterile, conical centrifuge tubes. Cells were collected by centrifugation at approximately 800-1000×g for 5 minutes. Cells were resuspended and diluted to a concentration of $3\times10^6$ cells/ml, and seeded onto 0.4 micron pore size, 24 mm diameter tissue culture treated transwells in a six-well tray at a density of $3.0\times10^6$ cells/TW ($6.6\times10^5$ cells/$cm^2$). Cells were maintained overnight in a seed medium. The seed medium consisted of; a base 3:1 mixture of DMEM, Hams F-12 medium (Quality Biologics, Gaithersburg, Md.), 4 mM GlutaMAX (Gibco BRL, Grand Island, N.Y.) and additives: 5 ng/ml human recombinant epidermal growth factor (Upstate Biotechnology Lake Placid, N.Y.), 0.4 µg/ml hydrocortisone (Sigma St. Louis, Mo.), $1\times10^{-4}$M ethanolamine (Fluka, Ronkonkoma, N.Y. ACS grade), $1\times10^{-4}$ M o-phosphoryl-ethanolamine (Sigma, St. Louis, Mo.), 20 pM triiodothyronine (Sigma, St. Louis, Mo.), and 6.78 ng/ml selenium (Sigma Aldrich Fine Chemicals Co., Milwaukee, Wis.), 50 ng/ml L-ascorbic acid (WAKO Pure Chemical Company), 0.2 µg/ml L-proline (Sigma, St. Louis, Mo.), and 0.1 µg/ml glycine (Sigma, St. Louis, Mo.). The cells were maintained in an incubator at 37±1° C. with an atmosphere of 10±1% $CO_2$ and fed fresh production medium every 2-3 days for 7 days. The production medium was composed of: a base 3:1 mixture of DMEM, Hams F-12 medium (Quality Biologics, Gaithersburg, Md.), 4 mM GlutaMAX (Gibco BRL, Grand Island, N.Y.) and additives: 5 ng/ml human recombinant epidermal growth factor (Upstate Biotechnology, Lake Placid, N.Y.), 2% newborn calf serum (Hyclone, Logan, Utah), 0.4 μg/ml hydrocortisone (Sigma St. Louis, Mo.), $1\times10^{-4}$ M ethanolamine (Fluka, Ronkonkoma, N.Y. ACS grade), $1\times10^{-4}$ M o-phosphoryl-ethanolamine (Sigma, St. Louis), 5 μg/ml insulin (Sigma, St. Louis, Mo.), 5 μg/ml transferrin (Sigma, St. Louis, Mo.), 20 pM triiodothyronine (Sigma, St. Louis, Mo.), and 6.78 ng/ml selenium (Sigma Aldrich Fine Chemicals Co., Milwaukee, Wis.), 50 ng/ml L-ascorbic acid (WAKO Pure Chemical Company), 0.2 μg/ml L-proline (Sigma, St. Louis, Mo.), 0.1 μg/ml glycine (Sigma, St. Louis, Mo.) and 0.05% poly-ethylene glycol (PEG) (Sigma, St. Louis, Mo.) cell culture grade. After 7 days the media was replaced with production medium without newborn calf serum. This media was fed fresh to the cells every 2-3 days for 20 more days, for a total of 28 days in culture.

Samples were taken at day 21 and fixed in formalin, then embedded in paraffin. The formalin fixed samples were embedded in paraffin and 5 micrometer section were stained with hematoxylin-eosin (H&E) according to techniques customarily used in the art. Using H&E stained slides, measurements were made at ten randomly picked microscopic fields utilizing a 10× Eyepiece (Olympus America Inc., Melville, N.Y.) loaded with a 10 mm/100 micrometer reticle (Olympus America Inc., Melville, N.Y.). The sample exhibited a structure composed of cells and matrix with a measured thickness of 71.20±9.57 microns. Besides endogenously produced fibrillar collagen, decorin and glycosaminoglycan were also present in the cell-matrix construct.

Example 12

In Vitro Formation of a Bilayer Skin Construct Containing Cells of Dermal Papilla A cell-matrix was made according to the method in Example 1 using Human Neonatal Foreskin Fibroblasts as a first matrix producing cell type. The cell-matrix was locally seeded with spots of dermal papilla cells as a second cell population which was in turn seeded with keratinocytes as a third cell population, to form a continuous epidermal layer over the cell-matrix and the dermal papilla cells.

First, a cell-matrix construct was formed using human dermal fibroblasts (HDF) derived from neonatal foreskin. HDF were scaled up by seeding them at $5\times10^5$ cells/162 cm$^2$ tissue culture treated flask (Costar Corp., Cambridge, Mass.) in growth medium consisting of: Dulbecco's Modified Eagle's medium (DMEM) (high glucose formulation, without L-glutamine, BioWhittaker, Walkersville, Md.) supplemented with 10% newborn calf serum (NBCS) (HyClone Laboratories, Inc., Logan, Utah) and 4 mM L-glutamine (BioWhittaker, Walkersville, Md.). When confluent, HDF were released from the plate using trypsin-versene and resuspended using fresh medium to a concentration of $3.0\times10^6$ cells/ml, and seeded onto 0.4 micron pore size, 24 mm diameter tissue culture treated inserts (TRANSWELL®, Corning Costar) in a six-well tray at a density of $3.0\times10^6$ cells/insert ($6.6\times10^5$ cells/cm$^2$). HDF cultures were maintained in an incubator at 37±1° C. with an atmosphere of 10±1% $CO_2$ and fed fresh production medium every 2 to 3 days for 23 days according the method detailed in Example 1.

After the cell-matrix construct had formed, it was seeded with spots of dermal papillae cells as a second cell population. Dermal papilla cells are a discrete population of specialized fibroblasts surrounded by the hair bulb of hair follicles to play a support role in the hair growth. Dermal papillae can be isolated by microdissecting hair follicles and cultured in vitro using the method previously described by Messenger, A. G., The Culture of Dermal Papilla Cells from Human Hair Follicles. Br. J. Dermatol. 110: 685-9 (1984), the method of which is incorporated herein. When a culture of dermal papilla cells reach confluence they form aggregates that can be replated on culture flasks to reform new aggregates. Dermal papillae were isolated from a skin biopsy obtained from a 4-week old pig. Cells from the dermal papilla (PDP) were serially cultured in DMEM containing 20% of NBCS until passage 8. After 3 weeks in culture, the PDP cells reformed dermal papilla-like structures, or aggregates, that each had a diameter approximately between 90 to 210 microns. The aggregates were then removed from the culture plate by vigorous pipetting of medium against them, and then seeded onto the Human Collagenous Matrix at the density of 200 aggregates per cm$^2$. The aggregates were cultured submerged for an additional 15 days in DMEM 20% NBCS with spent medium exchanged with fresh medium every 2-3 days.

The cell-matrix cultures containing dermal papilla cells thereon were seeded with keratinocytes and cultured to form a continuous epidermal layer over the cell-matrix and the dermal papillae. Two different constructs were made: the first with human keratinocytes, the second with pig keratinocytes. Normal epidermal keratinocytes were isolated from human neonatal foreskin (HEP), or from pig keratinocytes (PEP) using explant outgrowth to establish primary cultures. These cells were then cultured and expanded until passage 3 for the pig strain, or until passage 4 for the human strain. After about 5 to 6 days in culture, cells were then released from the culture dishes using trypsin-versene, pooled, centrifuged to form a cell pellet, resuspended in epidermalization medium, counted and seeded on top of the membrane at a density of $4.5\times10^4$ cells/cm$^2$ for HEP cells, or $1.6\times10^5$ cells/cm$^2$ for PEP cells. Epidermalized cultures were cultured for 12 days as previously described in Example 2.

Final samples were submitted for hematoxylin and eosin processing for light microscopy. The resulting skin constructs exhibited the basic morphological organization similar to skin: a dermal layer consisting of fibroblasts surrounded by endogenously produced matrix, including endogenously produced fibrillar collagen, decorin and glycosaminoglycan, localized areas of dermal papilla cells and a continuous, stratified layer of keratinocytes across the cell-matrix construct and the dermal papillae. In both tissue constructs overlaid with either human or pig keratinocytes, the dermal papilla maintained a packed structure that induced small undulations of the overlaid epithelium. Differentiated epithelial cells are often present close to the dermal papilla cells.

Example 13

Hyaluronic Acid Measurement by Sandwich ELISA

Hyaluronic acid (HA) was measured in cell-matrix constructs formed by dermal fibroblasts in serum-containing medium and chemically defined medium according to the methods of Examples 1 and 3, respectively.

Cell-matrix constructs were formed on circular 75 mm diameter carriers incorporating a porous membrane (TRANSWELL®, CorningCostar). Extracts from the cell-matrix constructs were prepared by adding 10 mL ammonium acetate buffer and 0.5 mg/mL Proteinase K to a test-tube tube containing a cell-matrix construct. The mixture was incubated at 60° C. overnight. After completion of digestion, the mixture was spun down and the supernatant extract was transferred to a separate tube for hyaluronic acid assay. A 96-well plate was coated with 50 μL of 20 μg/mL HA binding protein in 0.1 M NaHCO$_3$ solution and stored overnight at 4° C. The plate was then washed three times with 0.85% NaCl containing 0.05% Tween 20. To each well was then added 250 μL blocking solution (sodium phosphate buffer, 10 mmol, pH=7.4 containing 3% BSA and 0.9% NaCl, PBS+3% BSA) and the plate was incubated at RT for 2 h. The plate was then washed three times with 0.85% NaCl containing 0.05% Tween 20. To the plate was then added 50 μL of standard HA solutions and extracts from both experimental conditions, including various dilutions of these conditions. The plate was incubated at room temperature (about 20° C.) for 2 hours. The plate was then washed three times with 0.85% NaCl containing 0.05% Tween 20 and to each well was added 50 μL of biotinylated HA (1:2000 dilution) and then incubated for 2 hours at room temperature. The plate was then washed three times with 0.85% NaCl containing 0.05% Tween 20 and then added to each well was 50 μL of HRP-avidin D (1:3000 dilution). The plate was then incubated for 45 minutes at room temperature. The plate was then washed three times with 0.85% NaCl containing 0.05% Tween 20 and to each well was added 100 μL of orthophenylenediamine substrate solution. The plate was incubated at 37° C. for 10 minutes. The reaction was stopped by addition of 50 μL of 1M HCl. Finally, using a plate reader, the absorbance was read at 492 nm and recorded.

Absorbance measurements were averaged and converted to quantity measures. Circular cell-matrix constructs (75 mm diameter) formed in a serum containing media were determined to each contain about 200 μg hyaluronic acid while those formed in chemically defined medium each contained about 1.5 mg hyaluronic acid.

Example 14

Physical Testing and Mechanical Properties of the Cell-Matrix Construct Produced The mechanical properties of the tissue constructs of Example 1 (cell-matrix construct), Example 2 (cell-matrix construct with a keratinocyte layer thereon), and Example 3 (cell-matrix construct formed in defined medium) were quantified by membrane inflation tests. These tests are similar to assays used clinically (e.g. Dermaflex®, Cyberderm Inc., Media, Pa., and Cutameter®, Courage Khazaka, Cologne, Germany) but involve higher pressures including pressures able to burst the membrane. The sample cell-matrix construct was laid flat on a polycarbonate block centered over a cylindrical well 10 mm in diameter filled with normotonic saline. A metal plate with a circular hole corresponding to the diameter of the cylindrical well was placed over the sample and clamped to the block. The samples were then inflated by infusing additional saline into the well with a syringe pump. The resulting pressure was measured with a pressure transducer. Pressurization was carried out until device failure, the burst strength, which averaged at 439.02 mm Hg for the cell-matrix construct generated by the method of Example 1; 998.52 mm Hg for the samples of the cell-matrix construct with a keratinocyte layer generated by the method of Example 2; and, 1542.26 mm Hg for the samples cell-matrix construct formed in defined medium generated according to the method of Example 3.

To determine the thermal melting point of the dermal matrix, samples (cell-matrix construct), taken at 21 days were prepared using procedure described in Example 1. The samples denaturation temperature was determined by analysis with Mettler Toledo (Highston, N.J.) differential scanning calorimeter (DSC product #DSC12E). For our purposes, the melting temperature was determined by heating the sample from 45 and 80° C. at a rate of 1° C./minute. The average denaturation temperature for the samples is 60.8±1.2° C. (n=3).

The suture retention and pull strength of the epidermalized matrix created using the procedures in Examples 1 (cell-matrix construct) and 3 (cell-matrix construct formed in defined medium) were measured to determine the suturability of the construct in certain clinical situations. Suture retention strength of the 21 day old human dermal matrix was determined using method described in American National standards publication for Vascular Graft Prosthesis (Instruments, 1986) using a Mini-Bionex 858 test system (MTS systems Corporation, Minneapolis, Minn.)

For the samples of Example 1, (cell-matrix construct), the tensile strength was determined to be 365 N/m; for samples prepared according to Example 2 (cell-matrix construct with a keratinocyte layer), the tensile strength was 2720 N/m.

The suture retention strength for samples prepared according to Example 1 was 0.14 N; for those prepared according to Example 2, 0.22 N.

The constructs created as described in Examples 1, 2 and 3 have been made in both 24 mm and 75 mm diameters. The constructs made by the culturing techniques of all 3 methods are cohesive tissue-like structures are easily peeled form the membrane with minimal force, hence "peelable", and able to be physically handled and manipulated for use and testing without damage occurring.

Example 15

In Vitro Formation of a Collagenous Matrix by Human Neonatal Foreskin Fibroblasts in Chemically Defined Medium Human neonatal foreskin fibroblasts were expanded using the procedure described in Example 1. Cells were then resuspended to a concentration of $3 \times 10^6$ cells/ml, and seeded on to 0.4 micron pore size, 24 mm diameter tissue culture treated membrane inserts in a six-well tray at a density of $3.0 \times 10^6$ cells/TW ($6.6 \times 10^5$ cells/cm$^2$). Cells in this example were cultured in chemically defined medium throughout.

The medium contained: a base 3:1 mixture of DMEM, Hams F-12 medium (Quality Biologics, Gaithersburg, Md.), 4 mM GlutaMAX (Gibco BRL, Grand Island, N.Y.) and additives: 5 ng/ml human recombinant epidermal growth factor (Upstate Biotechnology, Lake Placid, N.Y.), $1 \times 10^{-4}$ M ethanolamine (Fluka, Ronkonkoma, N.Y. cat. #02400 ACS grade), $1 \times 10^{-4}$ M o-phosphoryl-ethanolamine (Sigma, St. Louis, Mo.), 5 μg/ml transferrin (Sigma, St. Louis, Mo.), 20 pM triiodothyronine (Sigma, St. Louis, Mo.), and 6.78 ng/ml selenium (Sigma Aldrich Fine Chemicals Company, Milwaukee, Wis.), 50 ng/ml L-ascorbic acid (WAKO Chemicals USA, Inc.), 0.2 μg/ml L-proline (Sigma, St. Louis, Mo.), 0.1 μg/ml glycine (Sigma, St. Louis, Mo.).

To the basic medium above, other components were added in these separate Conditions:
1. 5 μg/ml insulin (Sigma, St. Louis, Mo.), 0.4 μg/ml hydrocortisone (Sigma, St. Louis, Mo.), 0.05% polyethylene glycol (PEG) (Sigma, St. Louis, Mo.).
2. 5 μg/ml insulin (Sigma, St. Louis, Mo.), 0.4 μg/ml hydrocortisone (Sigma, St. Louis, Mo.).
3. 375 μg/ml insulin (Sigma, St. Louis, Mo.), 6 μg/ml hydrocortisone (Sigma, St. Louis, Mo.).

Figure 2:
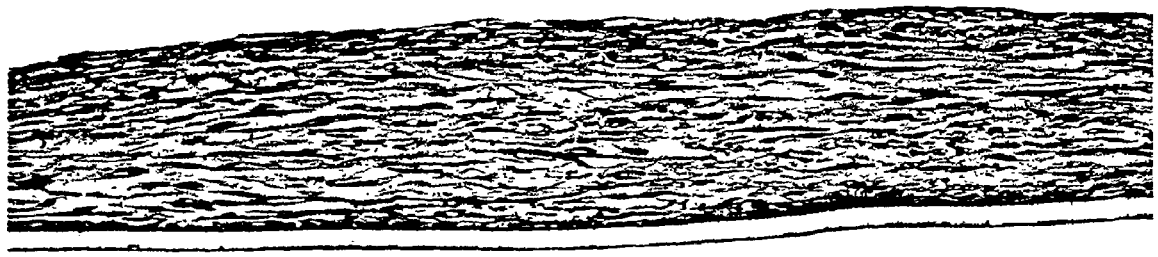
FIG. 2 is a photomicrograph (objective 20×) of a fixed, paraffin embedded, hematoxylin and eosin stained section of a cell-matrix construct formed from cultured human dermal fibroblasts in chemically defined medium at 21 days. The porous membrane appears as a thin translucent band below the construct.

Samples were formalin fixed and processed for hematoxylin and eosin staining for light microscope analysis. Visual histological evaluation demonstrated that the Condition 2 lacking PEG demonstrated a comparably similar matrix as Condition 1 containing PEG. Biochemical analysis measuring the collagen content of the construct showed nearly the same amount of collagen in both: 168.7±7.98 µg/cm² for Condition 1 with PEG as compared to 170.88±9.07 µg/cm² for Condition 2 without PEG. Condition 3 containing high levels of insulin and hydrocortisone showed a higher expression of matrix, including collagen, at a timepoint earlier than the other two conditions. Besides endogenously produced fibrillar collagen, decorin and glycosaminoglycan were also present in the cell-matrix constructs in all Conditions. The cultured dermal construct formed by the method of Condition 2 of this Example is shown in FIG. 2. Shown in FIG. 2 is a photomicrograph of a fixed, paraffin embedded, hematoxylin and eosin stained section of a cell-matrix construct formed from cultured human dermal fibroblasts in chemically defined medium at 21 days. The porous membrane appears as a thin translucent band below the construct and it can be seen that the cells grow on the surface of the membrane and do not envelope or integrate the membrane with matrix.

Figure 3:
FIG. 3 shows transmission electron microscope images of two magnifications of a cell-matrix construct formed from cultured human dermal fibroblasts in chemically defined medium at 21 days.
Figure 3:
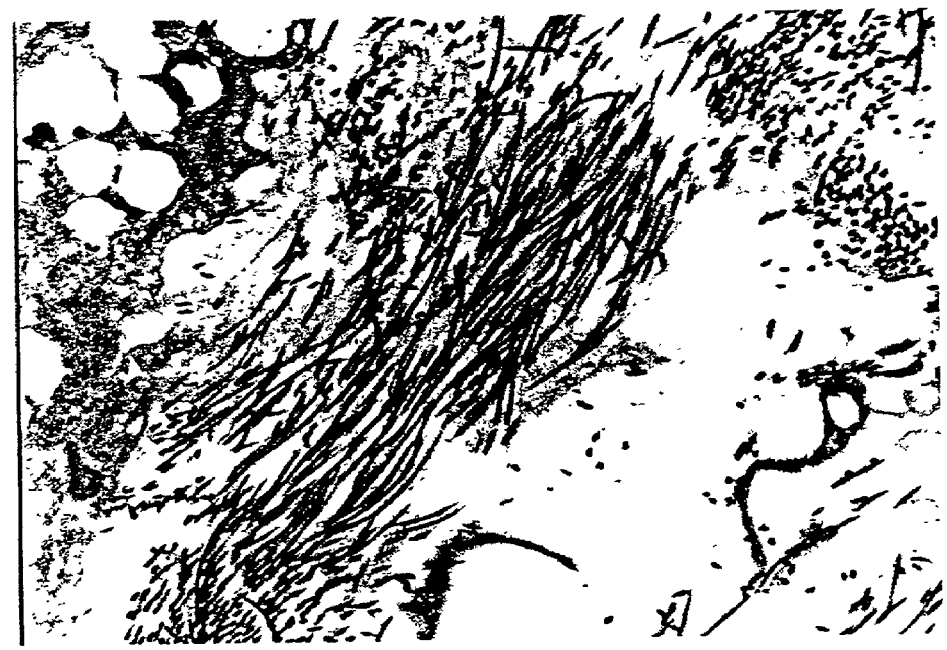

FIG. 3 shows transmission electron microscope (TEM) images of two magnifications of cultured dermal construct formed by the method of Condition 2 of this Example at 21 days. FIG. 3A is a 7600× magnification showing alignment of endogenous collagen fibers between the fibroblasts. FIG. 3B is a 1900× magnification of fully formed endogenous collagen fibers demonstrating fibril arrangement and packing.

In all Conditions of this Example, the cultured dermal constructs formed comprise dermal fibroblasts and endogenously produced matrix. All have fully formed collagen fibrils in packed organization arranged between the cells. Their fibrous qualities, thickness, and cohesive integrity give the construct considerable strength to allow it to be peelably removed from the culture membrane and handled as it is transferred to a patient to be treated with the construct, as in a graft or implant.

Example 16

Full Thickness Skin Construct

Using a 21 day dermal construct formed by human dermal fibroblasts under chemically defined conditions according to the method of Condition 2 (without PEG) described in Example 15, above, normal human neonatal foreskin epidermal keratinocytes were seeded on the top surface of the cell-matrix construct to form the epidermal layer of the skin construct.

The medium was aseptically removed from the culture insert and its surrounds. Normal human epidermal keratinocytes were scaled up to passage 4 from frozen subculture cell stock to confluence. Cells were then released from the culture dishes using trypsin-versene, pooled, centrifuged to form a cell pellet, resuspended in epidermalization medium, counted and seeded on top of the membrane at a density of $4.5 \times 10^{-4}$ cells/cm². The constructs were then incubated for 90 minutes at 37±1° C., 10% $CO_2$ to allow the keratinocytes to attach. After the incubation, the constructs were submerged in epidermalization medium. The epidermalization medium is composed of: a 3:1 base mixture of Dulbecco's Modified Eagle's Medium (DMEM) (containing no glucose and no calcium, BioWhittaker, Walkersville, Md.) and Hams F-12 medium (Quality Biologics Gaithersburg, Md.), supplemented with 0.4 µg/ml hydrocortisone (Sigma St. Louis, Mo.), $1 \times 10^{-4}$ M ethanolamine (Fluka, Ronkonkoma, N.Y.), $1 \times 10^{-4}$ M o-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 pM triiodothyronine (Sigma, St. Louis, Mo.), 6.78 ng/ml selenium (Aldrich), 24.4 µg/ml adenine (Sigma Aldrich Fine Chemicals Company, Milwaukee, Wis.), 4 mM L-glutamine (BioWhittaker, Walkersville, Md.), 50 µg/ml L-ascorbate sodium salt (Sigma Aldrich Fine Chemicals Company, Milwaukee, Wis.), 16 µM linoleic acid (Sigma, St. Louis, Mo.), 1 µM tocopherol Acetate (Sigma, St. Louis, Mo.) and 50 µg/ml gentamicin sulfate (Amersham, Arlington Heights, Ill.). The constructs were cultured in the epidermalization medium for 2 days at 37±1° C., 10±1% $CO_2$.

After 2 days the medium was exchanged with fresh medium composed as above, and returned to the incubator set at 37±1° C., 10±1% $CO_2$ for 2 days. After the 2 days, the carrier containing the construct was aseptically transferred to new culturing trays with sufficient media to achieve a fluid level just to the surface of the carrier membrane to maintain the developing construct at the air-liquid interface. The air contacting the top surface of the forming epidermal layer allows stratification of the epithelial layer. The constructs were incubated at 37±1° C., 10% $CO_2$, and low humidity, in media with media changes every 2-3 days for 7 days. This medium contained a 1:1 mixture of Dulbecco's modified Eagle's medium (DMEM) (containing no glucose and no calcium, BioWhittaker, Walkersville, Md.), Hams F-12 medium (Quality Biologics, Gaithersburg, Md.), supplemented with 0.4 µg/ml hydrocortisone (Sigma, St. Louis, Mo.), $5 \times 10^{-4}$ M ethanolamine (Fluka, Ronkonkoma, N.Y.), $5 \times 10^{-4}$ M o-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 pM triiodothyronine (Sigma, St. Louis, Mo.), 6.78 ng/ml selenium (Sigma Aldrich Fine Chemicals Company), 24.4 µg/ml adenine (Sigma Aldrich Fine Chemicals Company), 4 mM L-glutamine (BioWhittaker, Walkersville, Md.), 2.65 µg/ml calcium chloride (Mallinckrodt, Chesterfield, Mo.), 16 µM linoleic acid (Sigma, St. Louis, Mo.), 1 µM tocopherol acetate (Sigma, St. Louis, Mo.), 1.25 mM serine (Sigma, St. Louis, Mo.), 0.64 mM choline chloride (Sigma, St. Louis, Mo.) and 50 µg/ml gentamicin sulfate (Amersham, Arlington Heights, Ill.). The cultures were fed every 2-3 days, for 14 days.

Figure 4:
FIG. 4 is a photomicrograph (objective 20×) of a fixed, paraffin embedded, hematoxylin and eosin stained section of a cultured skin construct formed in chemically defined media in the absence of exogenous matrix components comprising a cell-matrix construct formed from cultured human dermal fibroblasts in chemically defined medium with a multilayered, differentiated epidermis formed from cultured human keratinocytes in chemically defined medium.

Samples, in triplicate, were submitted 10, 12, and 14 days after the construct was lifted to the air-liquid interface for hematoxylin and eosin processing as described in Example 1 to determine gross appearance under light microscopy. The resulting construct was a bilayer skin construct consisted of a lower dermal layer consisting of dermal fibroblasts surrounded by matrix overlaid by an upper epidermal layer of stratified and differentiated keratinocytes. The bilayer skin construct of this Example is shown in FIG. 4. FIG. 4 is a photomicrograph of a fixed, paraffin embedded, hematoxylin and eosin stained section of a cultured skin construct formed in chemically defined media in the absence of exogenous matrix components comprising a cell-matrix construct formed from cultured human dermal fibroblasts in chemically defined medium with a multilayered, differentiated epidermis formed from cultured human keratinocytes in chemically defined medium.

Example 17

Formation of a Collagenous Matrix by Human Buccal Fibroblasts

The purpose of this experiment is to produce a cell-matrix construct from buccal fibroblasts isolated from human cheek tissue. Buccal were cultured in T-150 flasks in DMEM containing 10% NBCS medium. After 7 days, to expand the number of cells further, buccal cells were harvested and passaged into nine T-150 flasks at $4.0 \times 10^6$ cells in DMEM containing 10% NBCS medium and cultured until confluence at which time the cells were harvested.

To harvest the cells, the medium was aspirated from the culture flask. To rinse the monolayer, sterile-filtered phosphate buffered saline was added to the bottom of each culture flask and then aspirated from the flasks. Cells were released from the flask by adding 5 mL trypsin-versene glutamine (BioWhittaker, Walkersvile, Md.) to each flask and gently rocking to ensure complete coverage of the monolayer. Cultures were returned to the incubator. As soon as the cells were released 5 ml of SBTI (Soybean Trypsin Inhibitor) was added to each flask and mixed with the suspension to stop the action of the trypsin-versene. The cell suspension was removed from the flasks and evenly divided between sterile, conical centrifuge tubes. Cells were collected by centrifugation at approximately 800-1000×g for 5 minutes.

Cells were resuspended using fresh medium to a concentration of $3.0 \times 10^6$ cells/ml, and seeded onto 0.4 micron pore size, 24 mm diameter tissue culture treated inserts (TRANSWELL®, Corning Costar) in a six-well tray at a density of $3.0 \times 10^6$ cells/insert ($6.6 \times 10^5$ cells/cm$^2$). The cells were maintained in an incubator at $37 \pm 1°$ C. with an atmosphere of $10 \pm 1\%$ CO$_2$ and fed medium containing: a base 3:1 mixture of DMEM, Hams F-12 medium (Quality Biologics, Gaithersburg, Md.), 4 mM GlutaMAX (Gibco BRL, Grand Island, N.Y.) and additives: 5 ng/ml human recombinant epidermal growth factor (Upstate Biotechnology, Lake Placid, N.Y.), 0.4 µg/ml hydrocortisone (Sigma, St. Louis, Mo.), $1 \times 10^{-4}$ M ethanolamine (Fluka, Ronkonkoma, N.Y. cat. #02400 ACS grade), $1 \times 10^{-4}$ M o-phosphoryl-ethanolamine (Sigma, St. Louis, Mo.), 5 µg/ml insulin (Sigma, St. Louis, Mo.), 5 µg/ml transferrin (Sigma, St. Louis, Mo.), 20 pM triiodothyronine (Sigma, St. Louis, Mo.), and 6.78 ng/ml selenium (Sigma Aldrich Fine Chemicals Company, Milwaukee, Wis.), 50 ng/ml L-ascorbic acid (WAKO Chemicals USA, Inc.), 0.2 µg/ml L-proline (Sigma, St. Louis, Mo.), 0.1 µg/ml glycine (Sigma, St. Louis, Mo.) and 0.05% poly-ethylene glycol (PEG) (Sigma, St. Louis, Mo.).

At day 1 post seeding, medium was replaced with Serum Free Production Media, exchanged every 2-3 days for 21 days. At day 21, samples were fixed in formalin for histology. Three samples were used for protein and collagen production analysis.

Collagen production for 24 mm diameter constructs averaged 519 µg per construct after 21 days in culture. Total protein production for 24 mm diameter constructs averaged 210 µg per construct after 21 days in culture. Morphologically, the buccal fibroblast cell-matrix construct, a cultured tissue construct of oral connective tissue, showed buccal fibroblasts surrounded by matrix while physically, the construct had physical bulk and integrity.

Although the foregoing invention has been described in some detail by way of illustration and Examples for purposes of clarity and understanding, it will be obvious to one of skill in the art that certain changes and modifications may be practiced within the scope of the appended claims.

We claim:

1. A method for producing a cultured tissue construct, comprising,
   (a) seeding human fibroblast cells capable of synthesizing an extracellular matrix on a porous membrane, wherein the membrane comprises pores that are about 3 microns or less in size, in a culture vessel in a chemically defined cell culture medium, wherein the chemically defined cell culture medium is free of undefined animal organ or tissue extracts and comprises the following:
      (i) nutrient base medium;
      (ii) insulin;
      (iii) L-glutamine or an L-glutamine derivative; and
      (iv) ascorbate or an ascorbate derivative;
   (b) stimulating the fibroblast cells, which are at least at 80% confluence to synthesize, secrete and organize extracellular matrix components; and,
   (c) continued culturing of the fibroblast cells to thereby produce a cultured tissue construct with an extracellular matrix of at least about 30 microns thick and cultured fibroblast cells contained within the synthesized extracellular matrix layer, wherein the extracellular matrix comprises:
      (i) fibrillar collagen showing a packing organization of fibrils and fibril bundles exhibiting a quarter-staggered 67 nm banding pattern;
      (ii) tenascin; and,
      (iii) glycosaminoglycans;
   and wherein said extracellular matrix is produced by the cultured fibroblast cells on one surface of the porous membrane.

2. The method of claim 1, wherein the human fibroblast cells are dermal cells.

3. The method of claim 1, wherein the ascorbate derivative is selected from the group consisting of sodium ascorbate, ascorbic acid and L-ascorbic acid phosphate magnesium salt n-hydrate.

4. The method of claim 1, wherein the nutrient base medium is selected from the group consisting of Dulbecco's Modified Eagle's Medium (DMEM), Minimal Essential Medium (MEM), M199, RPMI 1640, Iscove's Modified Dulbecco's Medium (EDMEM), Ham's F-12, Ham's F-10, NCTC 109, and NCTC 135 nutrient base media.

5. The method of claim 1, wherein the L-glutamine derivative is L-alanyl-L-glutamine.

* * * * *